US012768838B2

(12) United States Patent
Blaire et al.

(10) Patent No.: US 12,768,838 B2
(45) Date of Patent: Oct. 20, 2026

(54) KIT AND METHOD FOR CAPTURING A MOLECULE WITH MAGNETIC MEANS

(71) Applicants: CENTRE NATIONAL DE LA RECHERCHE SCIENTIFIQUE, Paris (FR); INSTITUT POLYTECHNIQUE DE GRENOBLE, Grenoble Cedex (FR)

(72) Inventors: Guillaume Blaire, Magland (FR); Orphée Cugat, Poisat (FR); Victor Vieille, Vimines (FR)

(73) Assignees: CENTRE NATIONAL DE LA RECHERCHE SCIENTIFIQUE, Paris (FR); INSTITUT POLYTECHNIQUE DE GRENOBLE, Grenoble (FR)

( * ) Notice: Subject to any disclaimer, the term of this patent is extended or adjusted under 35 U.S.C. 154(b) by 1039 days.

(21) Appl. No.: 17/638,501

(22) PCT Filed: Aug. 31, 2020

(86) PCT No.: PCT/EP2020/074233
§ 371 (c)(1),
(2) Date: Feb. 25, 2022

(87) PCT Pub. No.: WO2021/038107
PCT Pub. Date: Mar. 4, 2021

(65) Prior Publication Data

US 2022/0412969 A1 Dec. 29, 2022

(30) Foreign Application Priority Data

Aug. 30, 2019 (FR) ....................................... 1909561

(51) Int. Cl.
*G01N 33/543* (2006.01)
*G01N 27/74* (2006.01)

(52) U.S. Cl.
CPC ..... *G01N 33/54326* (2013.01); *G01N 27/745* (2013.01)

(58) Field of Classification Search
None
See application file for complete search history.

(56) References Cited

U.S. PATENT DOCUMENTS

| | | | | |
|---|---|---|---|---|
| 6,479,302 | B1 | 11/2002 | Dremel | |
| 7,658,332 | B1 * | 2/2010 | Adams | G06K 19/02 235/488 |
| 2009/0065359 | A1 * | 3/2009 | Zhou | G01R 33/1269 204/660 |
| 2009/0139908 | A1 | 6/2009 | Zhou et al. | |
| 2010/0055758 | A1 | 3/2010 | Kapur et al. | |
| 2012/0045828 | A1 | 2/2012 | Davis et al. | |
| 2017/0335364 | A1 | 11/2017 | Movy et al. | |

FOREIGN PATENT DOCUMENTS

| | | | | |
|---|---|---|---|---|
| CN | 101142314 A | | 3/2008 | |
| CN | 202011883 U | | 10/2011 | |
| CN | 107209180 A | | 9/2017 | |
| WO | WO-2014004577 A1 | * | 1/2014 | B01L 3/502761 |
| WO | 2014111187 A1 | | 7/2014 | |
| WO | 2017030999 A1 | | 2/2017 | |

OTHER PUBLICATIONS

Yangguang Resin Chemical Co.,Ltd (retrieved online https://www.ygresin.com/product/umoh-vinyl-resin/ on Apr. 22, 2025). (Year: 2025).*
Li et al. Scientific Reports | 7: 9894 | DOI:10.1038/s41598-017-09897-5 (Year: 2017).*
Office Action issued on Aug. 26, 2023, in corresponding Chinese Application No. 202080059384.8, 18 pages.
"Remanence", Wikipedia, https://en.wikipedia.org/w/index.php?title=Remanence&oldid=907967715, Jul. 26, 2009, 4 pages.
International Search Report mailed on Nov. 4, 2020, in corresponding to International Application No. PCT/EP2020/074233; 6 pages (with English Translation).
L. Coudron et al., "Low-cost credit card-based microfluidic devices for magnetic bead immobilisation"; Microfluid Nanofluid, Springer; vol. 14; No. 1-2; Sep. 18, 2012; XP035166850; pp. 359-369.
Martin A. M. Gijs; "Magnetic bead handling on-chip: new opportunities of analytical applications"; Microfluid Nanofluid; 2004; vol. 1; pp. 22-40.
Mark Tondra et al., "Design of Integrated Microfluidic Device for Sorting Magnetic Beads in Biological Assays"; 2001; 4 pages.
David Issadore et al., "Self-assembled magnetic filter for highly efficient immunomagnetic separation"; The Royal Society of Chemistry Lab Chip 2011; vol. 11; pp. 147-151; XP55049322.

* cited by examiner

*Primary Examiner* — Christopher L Chin
*Assistant Examiner* — Fernando Ivich
(74) *Attorney, Agent, or Firm* — Maier & Maier, PLLC

(57) ABSTRACT

A kit and a method for capturing a molecule contained in a sample utilizing at least one magnetic layer including a, possibly repeated, juxtaposition of at least one first and one second region, the first region including magnetic particles polarized in a first direction and the second region including magnetic particles that are non-polarized or polarized in a second direction different from the first direction of polarization of the magnetic particles of the first region, so as to generate a magnetic field having at least one variation in intensity of at least 0.1 mT at a distance of at least 1 μm from the at least one magnetic layer, the variation defining a maximum of the standard of the intensity of the magnetic field and level therewith a zone for capturing magnetic nanoparticles on the capture support.

14 Claims, 11 Drawing Sheets

[Fig. 1]
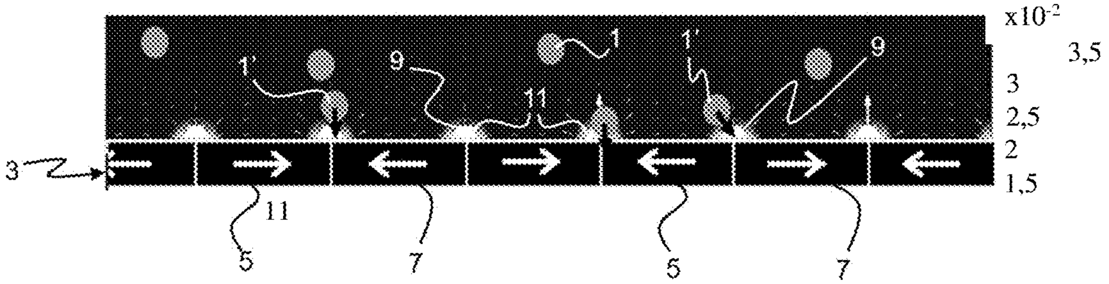
[Fig. 2]
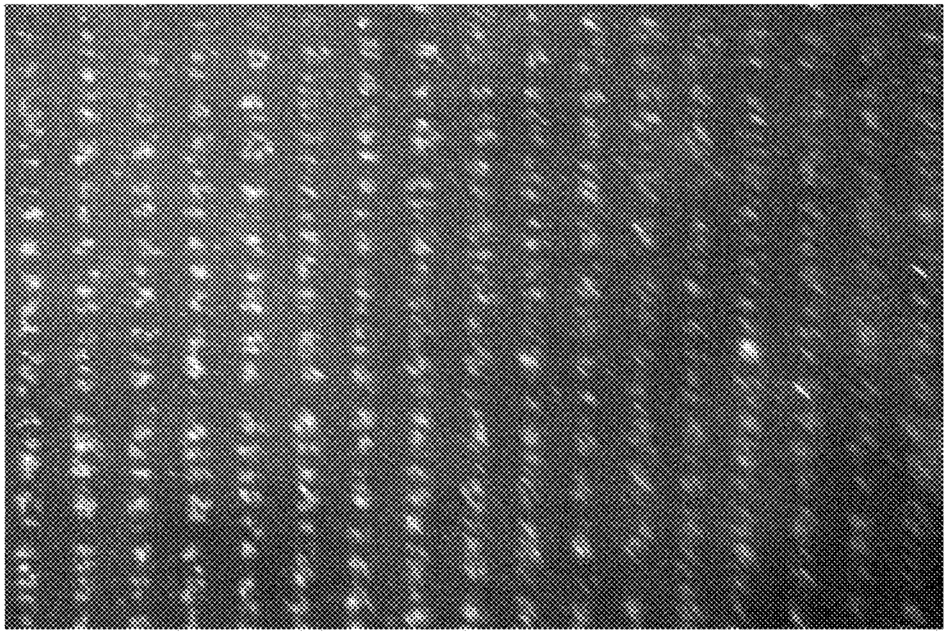

[Fig. 3]
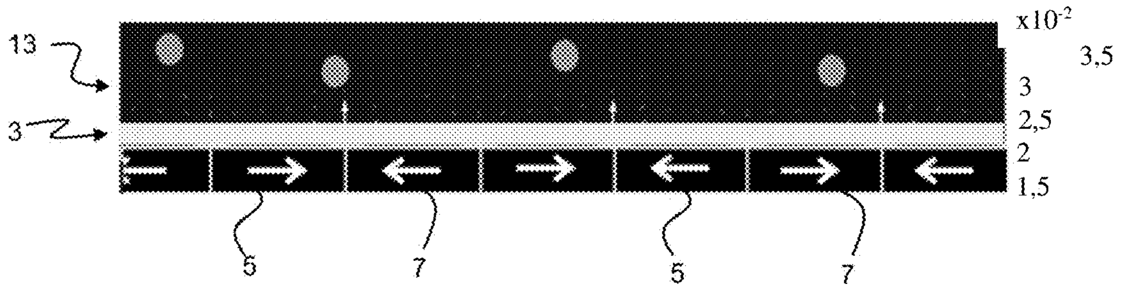
[Fig. 4]
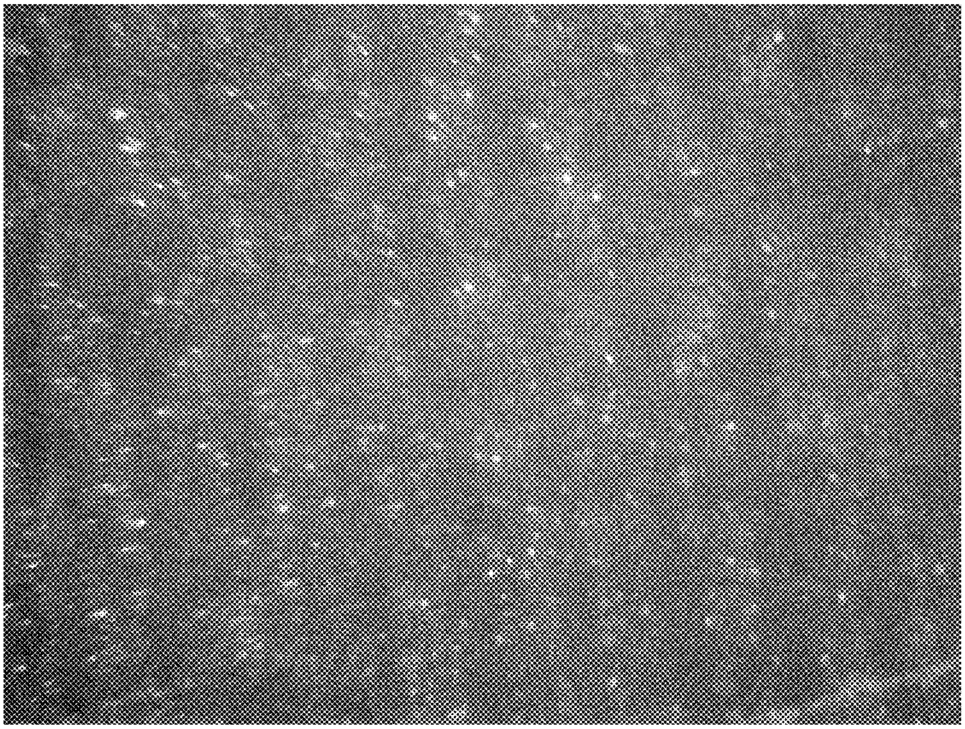

[Fig. 5a]
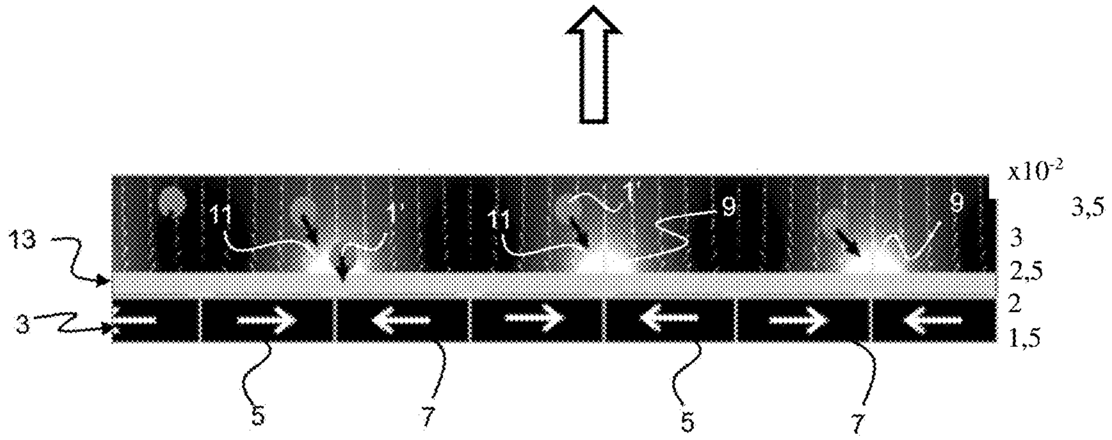
[Fig. 5b]
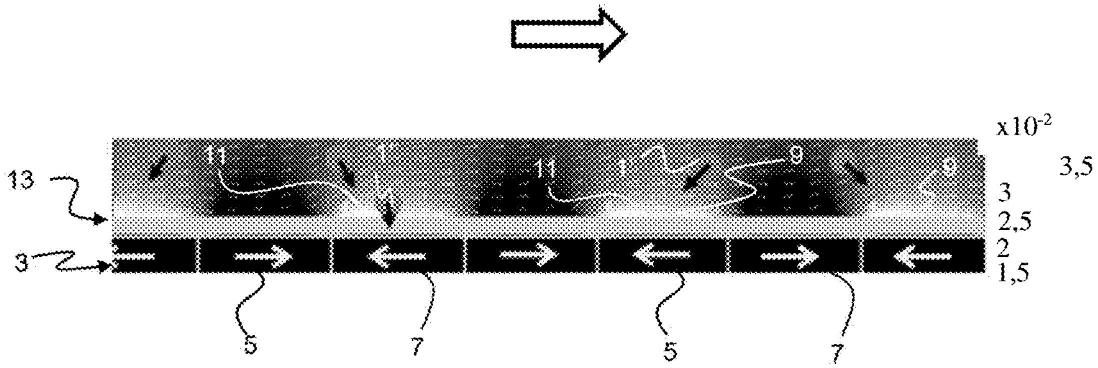

[Fig. 6]
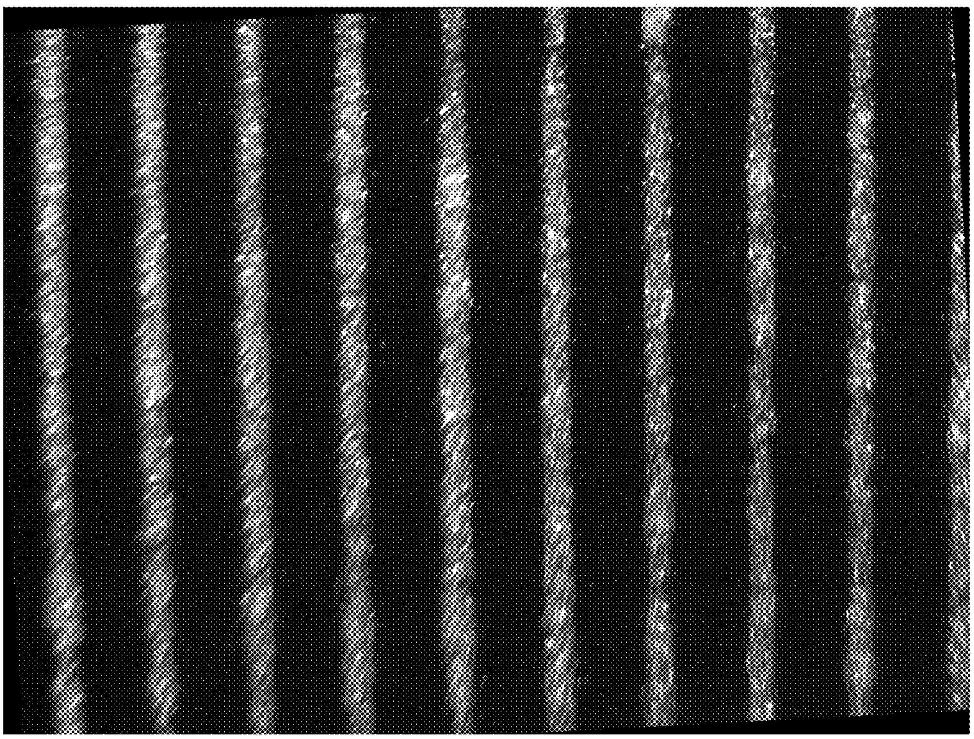

[Fig. 7]
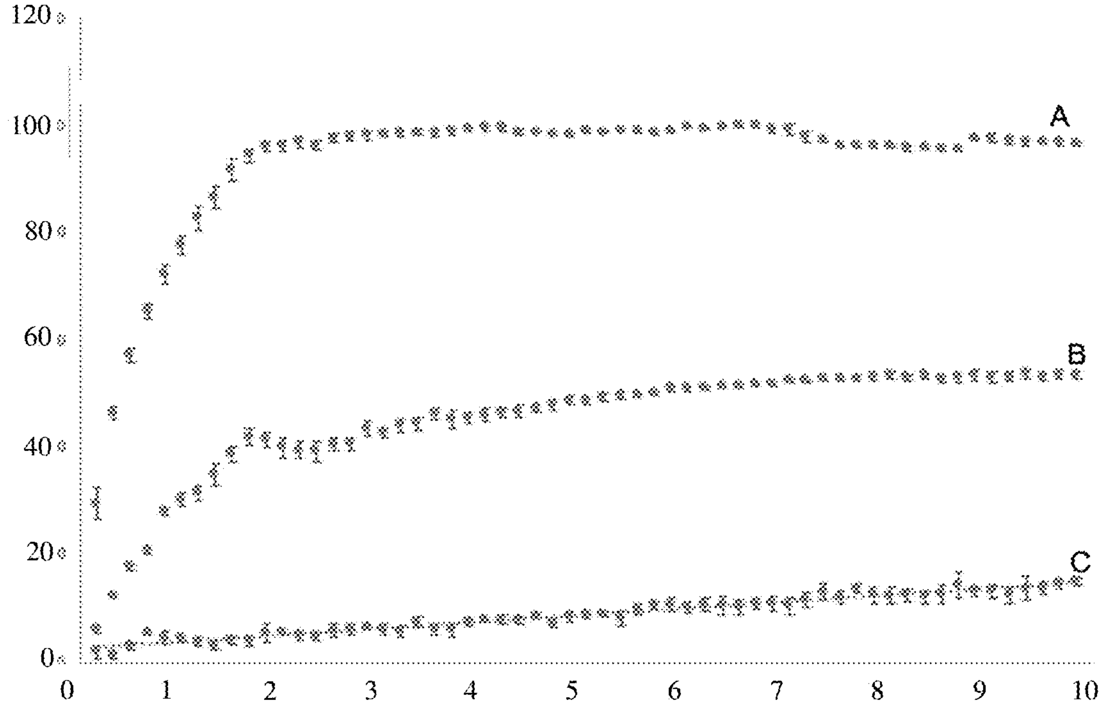

[Fig. 8]
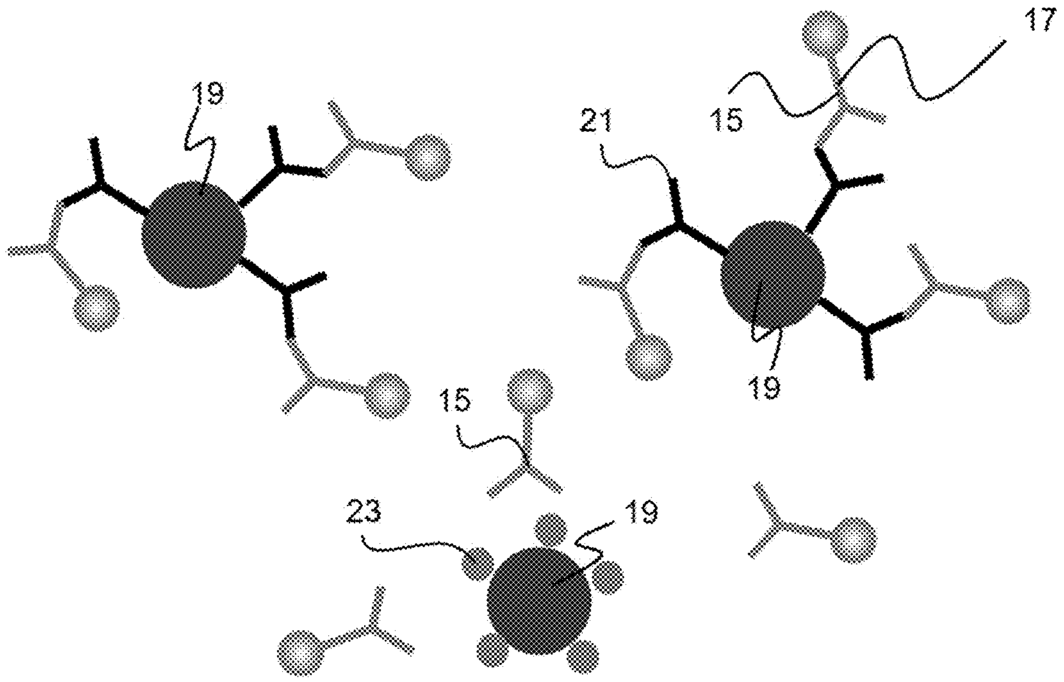
[Fig. 9]
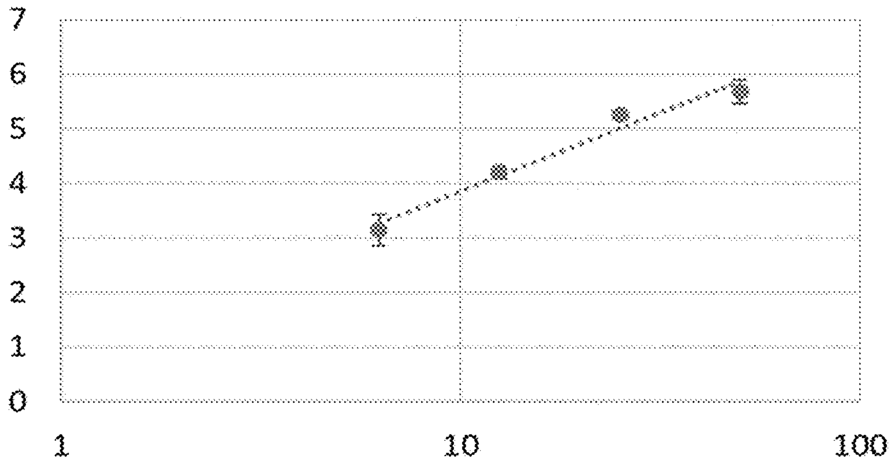

[Fig. 10]
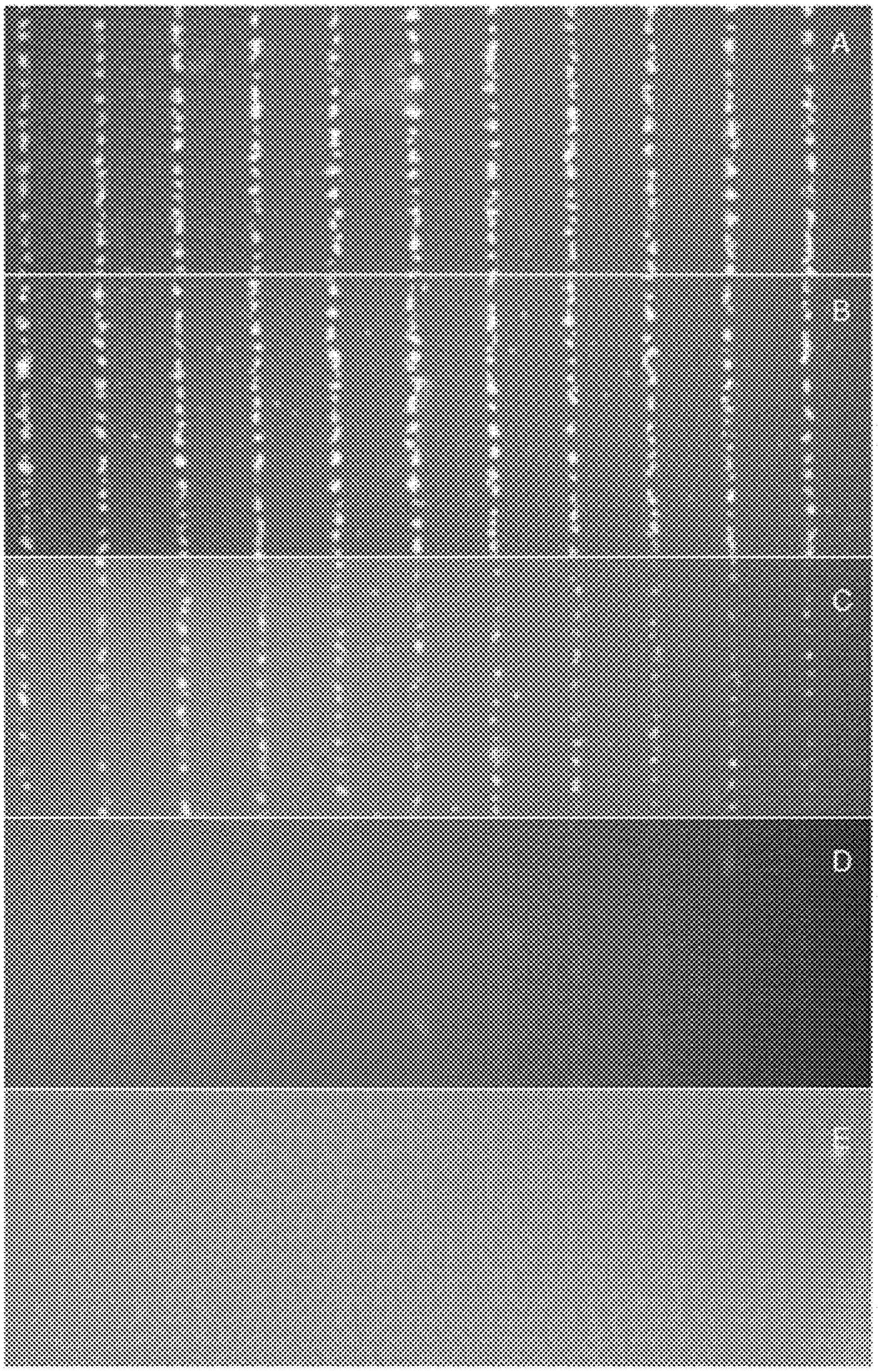

[Fig.11]
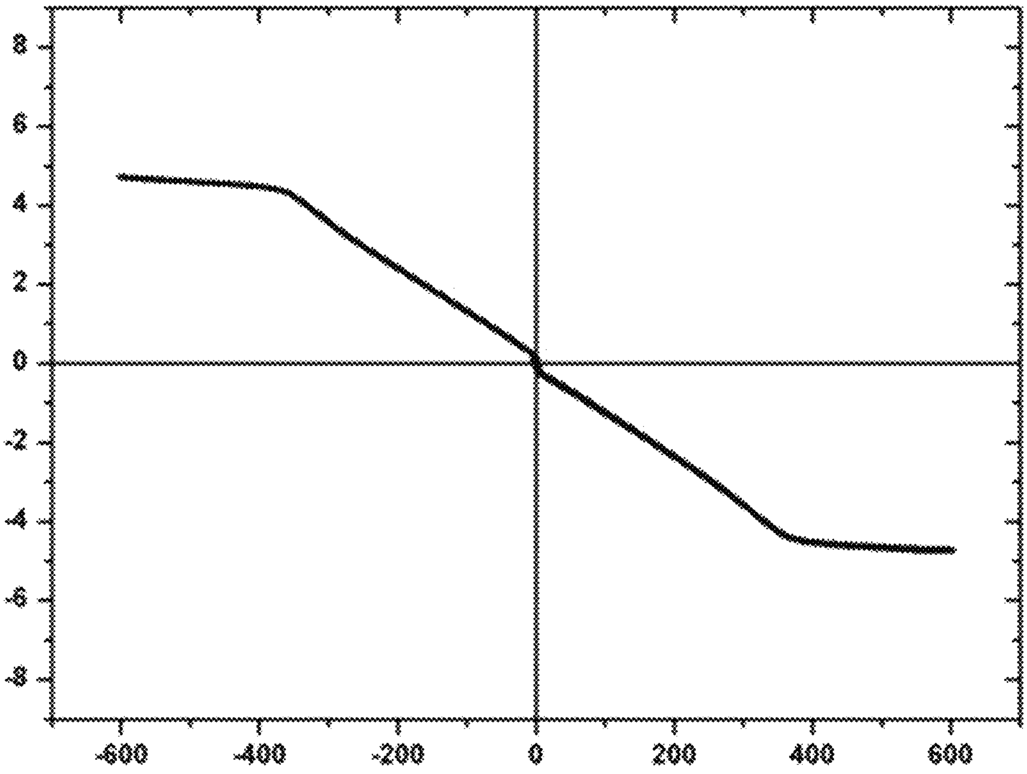

[Fig. 12]
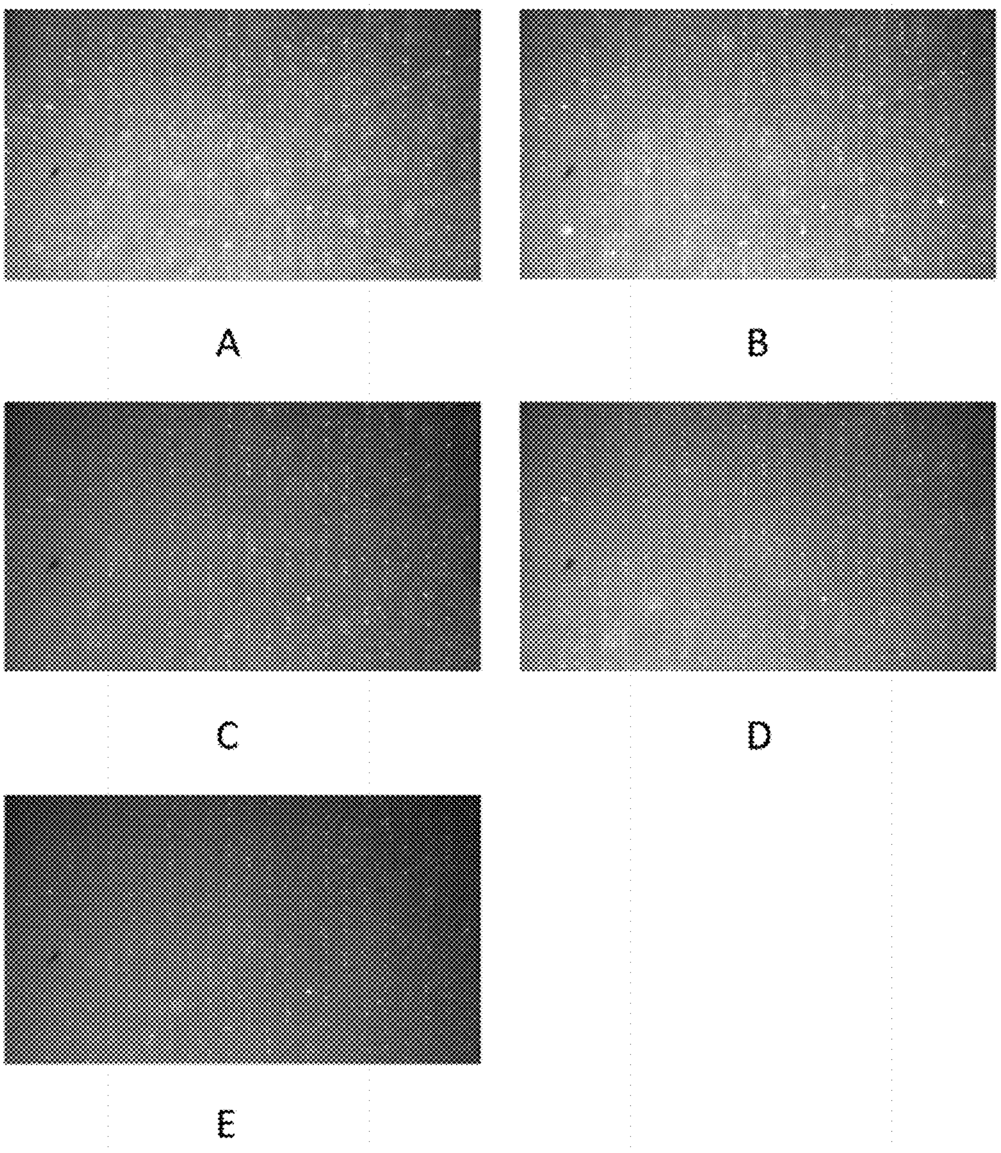

[Fig. 13]
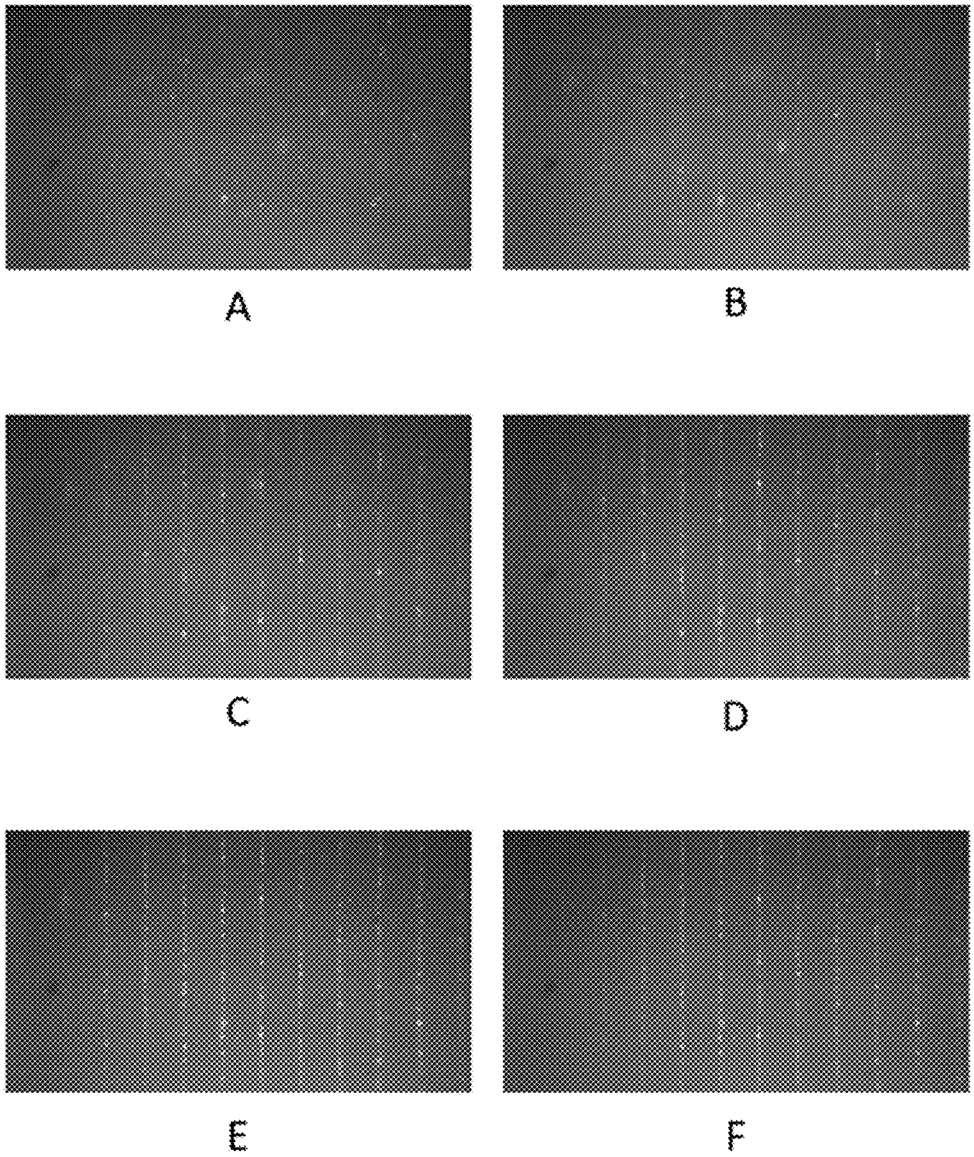

[Fig. 14]
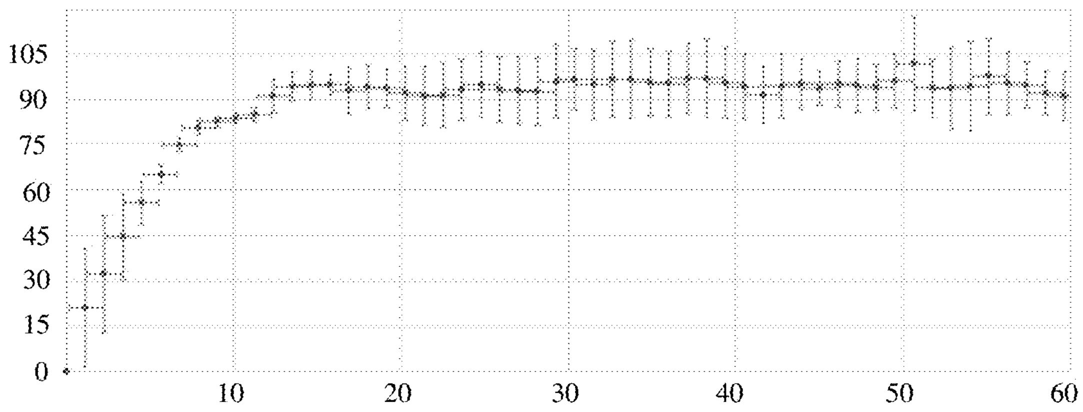
[Fig. 15]
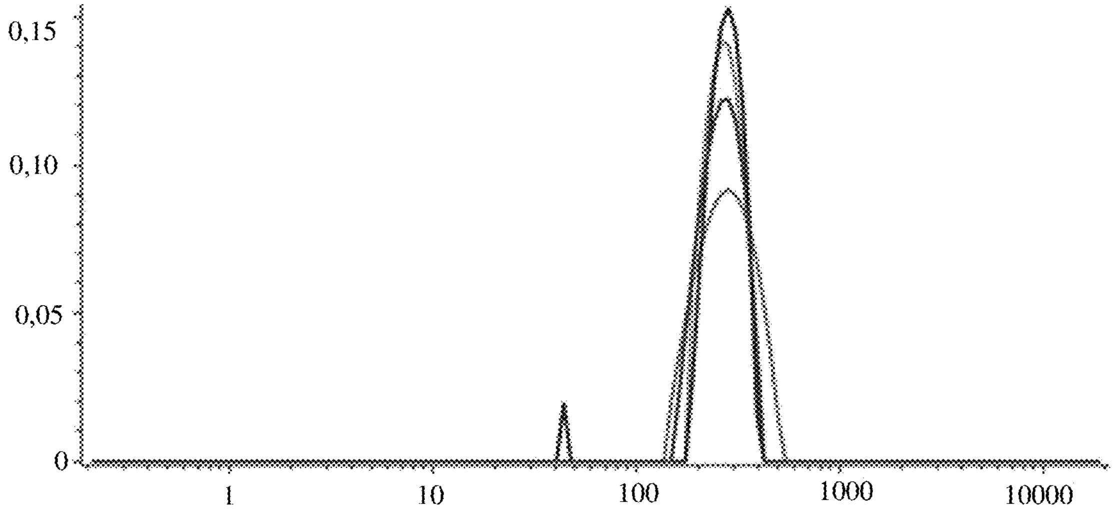

KIT AND METHOD FOR CAPTURING A MOLECULE WITH MAGNETIC MEANS

FIELD

The present invention relates to a kit for capturing a molecule. The invention also relates to a method for capturing a molecule.

BACKGROUND

The ELISA test (acronym for "Enzyme-Linked ImmunoSorbent Assay") is commonly used to quantitatively diagnose molecular markers (antigens, antibodies or the like) present in fluids, biopsies, cultures or any other sample.

However, this technique, which is currently the most robust and one of the most widespread of the diagnostic methods, has drawbacks, namely its complexity, the use of expensive automatons and its duration, which can reach several hours.

The ELISA test is a heterogeneous phase immunoassay technique, that is to say, it requires a solid support (typically, a titration plate comprising a plurality of wells) to which a suitable molecule is attached beforehand to capture the molecule to be assayed.

Once the molecule of interest has been captured on said support, washing makes it possible to remove the rest of the sample and to proceed to the step of detecting and quantifying said molecule.

For example, in the case of the so-called "sandwich" ELISA test, which allows an antigen to be assayed in a solution, the surface of the support is covered with a determined quantity of a so-called capture antibody, said antibody being suitable for binding to the desired antigen.

The solution capable of containing said antigen is then applied to the support; said antigen then binds to the capture antibody located on the surface of the support.

Then, the support is washed so as to remove any unbound antigen remaining in the solution. A solution containing an antibody called a detection antibody coupled to a detection means, which is adapted to bind to the antigen fixed on the support, is then deposited on the support. Said detection antibody can be marked directly and emit a detectable signal, but can also be coupled to an enzyme that will catalyze a substrate causing the emission of a detectable signal.

A new washing step is implemented, so as to keep the antigen bound to the detection antibody on the support, said antibody itself being coupled to the enzyme.

Finally, to detect and quantify the antigen, a substrate is deposited on the support that is converted by the enzyme into a detectable signal (for example a color analyzed spectroscopically, or by fluorescence emission) representative of the binding between the antigen and the detection antibody.

Said signal can be observed with the naked eye or by means of an instrument, such as a spectrophotometer.

The article by D. Issadore et al, Lab Chip, 2011, 11, 147 describes a method for capturing a molecule in a sample by circulating said sample in a fluidic microchannel arranged below a polydimethylsiloxane (PDMS) matrix in which NdFeB magnetic grains were immobilized.

Document WO2014111187 describes a method for capturing a molecule in a sample, comprising the following steps:—mixing said sample with magnetic particles, each of said particles being coupled with an element capable of selectively binding to said molecule to be captured, so as to form at least one complex comprising a magnetic particle, said element and said molecule bound to said element, and -immobilizing said at least one complex on a support comprising ordered magnetic field microsources.

These ordered magnetic field microsources are distributed in the vicinity of the surface of the support intended to be in contact with the sample according to a determined pattern and also have a determined magnetic orientation.

The method described in this document is interesting. However, the capture support is difficult to produce and to industrialize, in particular in a clean environment, which implies a high manufacturing cost.

SUMMARY

The object of the invention is in particular to overcome these drawbacks of the prior art.

More precisely, the object of the invention is to provide a kit and a method for capturing a molecule contained in a sample owing to high-performance magnetic means and having a reduced financial footprint compatible with low-cost production techniques.

Thus, the invention relates to a kit for capturing a molecule contained in a sample comprising:

a) magnetic nanoparticles having a largest dimension of less than 1 μm, said nanoparticles each being coupled to at least one capture element, said at least one capture element specifically binding to said molecule, and b) a support for capturing said magnetic nanoparticles comprising or consisting essentially of at least one magnetic layer, said magnetic layer comprising a juxtaposition, possibly repeated, of at least a first and a second region, the first region comprising magnetic particles polarized in a first direction, and the second region comprising magnetic particles that are non-polarized or polarized in a second direction different from the first direction of polarization of the magnetic particles of the first region, so that said at least one magnetic layer generates a magnetic field having at least one variation in intensity of at least 0.1 mT at a distance of at least 1 μm from said at least one magnetic layer, said at least one variation in intensity of the magnetic field defining a maximum and a minimum of the standard of the intensity of said magnetic field, so as to define, at said maximum of the standard of said magnetic field, a zone for capturing the magnetic nanoparticles on the capture support.

The inventors have discovered against all expectations that it is possible to attract nanoparticles coupled to a capture element using a magnetic layer having magnetic particles with weak magnetic properties.

The magnetic layers as used in the invention are flexible and correspond in particular to magnetic tapes. The magnetic layers of the invention are made up of magnetic composite materials, such as ferrites, randomly distributed in a polymer or else oriented along a preorientation axis. Ferrites are a ferromagnetic ceramic obtained by molding at high pressure and at high temperature (>1000° C.) from iron oxide $Fe_2O_3XO$, where X can be manganese, zinc, cobalt, nickel, barium, strontium, etc.

The invention thus consists in diverting the use of magnetic tapes commonly used for robust information storage (audio and video cassette, credit cards, badges, transport tickets, etc.), which are difficult to demagnetize, in order to apply them to the capture of nanometric magnetic particles in solution.

BRIEF DESCRIPTION OF THE FIGURES

FIG. 1 shows a capture of nanoparticles by a magnetic layer according to the invention. The capture system is shown in sectional view. The intensity of the magnetic fields emitted by the magnetic layer is defined by a color code whose scale is presented to the right of the sectional view (in T). The arrows in the magnetic layer represent the direction of the polarization of the grains composing it.

FIG. 2 shows a photograph of a capture by the system shown in FIG. 1. In this photograph, the white dots represent the nanoparticles.

FIG. 3 shows a capture of nanoparticles by a magnetic layer according to the invention, said layer being covered with a non-magnetic layer. The capture system is shown in sectional view. The intensity of the magnetic fields generated by the magnetic layer is defined by a color code whose scale is presented to the right of the sectional view (in T). The arrows from the nanoparticles represent the direction of movement of the nanoparticles attracted by the magnetic layer. The arrows in the magnetic layer represent the direction of the polarization of the grains composing it.

FIG. 4 shows a photograph of a capture by the system shown in FIG. 3. In this photograph, the white dots represent the nanoparticles.

FIG. 5*a* shows a capture of nanoparticles by a magnetic layer according to the invention, said layer being covered with a non-magnetic layer and the capture being carried out in the presence of the magnetic field from an additional source. The capture system is shown in sectional view. The direction of the magnetic field generated by the additional source is shown by the white arrow with a black border above the sectional view and is perpendicular to the magnetic layer. The intensity of the magnetic fields generated by the magnetic layer is defined by a color code whose scale is presented to the right of the sectional view (in T). The arrows from the nanoparticles represent the direction of movement of the nanoparticles attracted by the magnetic layer. The arrows in the magnetic layer represent the direction of the polarization of the grains composing it.

FIG. 5*b* shows a capture of nanoparticles by a magnetic layer according to the invention, said layer being covered with a non-magnetic layer and the capture being carried out in the presence of the magnetic field from an additional source. The capture system is shown in sectional view. The direction of the magnetic field generated by the additional source is shown by the white arrow with a black border above the sectional view and is parallel to the magnetic layer. The intensity of the total magnetic fields (generated by the magnetic layer and the additional source) is defined by a color code whose scale is presented to the right of the sectional view (in T). The arrows from the nanoparticles represent the direction of movement of the nanoparticles attracted by the magnetic layer. The arrows in the magnetic layer represent the direction of the polarization of the grains composing it.

FIG. 6 shows a photograph of a capture by the system shown in FIG. 5*a*. In this photograph, the white dots represent the nanoparticles.

FIG. 7 shows the percentage of nanoparticles captured (X axes) as a function of time (Y axes) for each capture of the captures shown in FIGS. 1 to 3. The time expressed in minutes. Curve A corresponds to the capture kinetics shown in FIG. 5*a*, curve B corresponds to the capture kinetics shown in FIG. 1, and curve C corresponds to the capture kinetics shown in FIG. 3.

FIG. 8 shows anti-mouse detection capture antibodies carrying a fluorochrome and coupled to nanoparticle complexes grafted with anti-mouse ovalbumin capture antibodies. It is also a nanoparticle grafted with ovalbumin.

FIG. 9 is a graph showing the amount of fluorescence calculated (arbitrary unit) as a function of the concentration of anti-ovalbumin antibody (ug/ml).

FIG. 10 shows photographs after capture of the complexes of FIG. 8. Each white point represents a fluorochrome carried by a capture antibody (anti-mouse) of FIG. 8. For FIG. 10A, a mouse antiovalbumin concentration of approximately 50 μg/ml was used; for FIG. 10B, a concentration of approximately 25 82 g/ml was used; for FIG. 10C, a concentration of approximately 12.5 μg/ml was used; for FIG. 10D, a concentration of approximately 6.25 μg/ml was used; FIG. 10E is a negative control without the use of anti-mouse ovalbumin antibodies.

FIG. 11 is a graph showing the calibration curve of a DLGi5 garnet in an MOIF system of the Mag View CMOS type. This graph shows the rotation of polarization of a light beam (in degrees) having passed through said garnet as a function of the intensity of the magnetic field (in Tesla).

FIG. 12 shows photographs after capture of nanoparticles in microfluidic chambers.

The white dots represent nanoparticles. A to E show capture kinematics (A: 0 seconds; B: 10 seconds; C: 30 seconds; D: 80 seconds and E: 120 seconds).

FIG. 13 shows photographs after capture of nanoparticles in microfluidic chambers in the presence of an additional magnetic field source. The white dots represent nanoparticles. A to F show capture kinematics (A: 0 seconds; B: 2 seconds; C: 5 seconds; D: 12 seconds; E: 34 seconds and F: 60 seconds).

FIG. 14 shows the percentage of captured nanoparticles (Y axes), as a function of time (X axes) for the capture shown in FIG. 12. The time is expressed in seconds.

FIG. 15 is a spectroscopic analysis graph showing the size of nanoparticles in solution.

The size was determined using the dynamic light scattering technique. The Y axis represents the relative frequency of nanoparticles as a percentage, and the X axis is a logarithmic scale representing the size of nanoparticles in nanometers.

DETAILED DESCRIPTION

For the sake of clarity for the remainder of the description, the magnetic particles making up a magnetic layer according to the invention will be called "powders" or "magnetic grains" so as to clearly distinguish them from "magnetic nanoparticles" coupled to the capture elements.

The magnetic layers of the invention are "encoded," that is to say, at least part of their constituent magnetic grains are polarized/magnetized. Hereinafter, the terms "polarized" and "magnetized" are taken as synonyms and will be used uniformly.

This encoding (or this polarization) is not carried out randomly, but is configured to reveal at least one juxtaposition of a first region comprising magnetic grains polarized in a first direction, and of a second region comprising magnetic grains that are non-polarized or polarized in a second direction different from the first direction of polarization of the magnetic grains, thereby defining at least one junction between a first and a second region. Each region (when polarized) therefore emits its own magnetic field, so that the magnetic layer can be modeled as a plurality of magnetic field sources.

The polarization of the magnetic grains making up said at least one magnetic layer is in particular carried out with a writing head that is well known in the field of magnetic tape encoding. Typically, a local magnetic field is applied to a region of a magnetic layer by means of a miniature electromagnet.

This particular juxtaposition of the first and second polarization regions makes it possible to create variations, at a distance of at least 1 μm from said at least one magnetic layer, in the intensity of the magnetic field generated, and therefore to create maximums and minimums of the standard of the intensity of the magnetic field. The standard of the intensity of the magnetic field corresponds to the absolute value of the intensity of the magnetic field (in Tesla). In the invention, the terms "standard of the intensity" and "standard" may be used instead. The maximums of the standard of the intensity of the magnetic field create zones that attract said suspended nanoparticles and in which said magnetic nanoparticles minimize their magnetic energy such that they are called "local minima" of the magnetic energy of the nanoparticles, or "energy sinks."

Thus, by orthogonal projection on the surface of said magnetic layer, the maximums of the standard of the intensity of the magnetic field will define capture zones of the nanoparticles. The capture zones and the energy sinks therefore coincide in the same place.

These capture zones extend over a distance of at most 35 μm from the orthogonal projection on the surface of said magnetic layer of the or each maximum of the standard of the intensity of the magnetic field. "At most 35 μm" means 35 μm, 34 μm, 33 μm, 32 μm, 31 μm, 30 μm, 29 μm, 28 μm, 27 μm, 26 μm, 25 μm, 24 μm, 23 μm, 22 μm, 21 μm, 20 μm, 19 μm, 18 μm, 17 μm, 16 μm, 15 μm, 14 μm, 13 μm, 12 μm, 11 μm, 10 μm, 9 μm, 8 μm, 7 μm, 6 μm, 5 μm, 4 μm, 3 μm, 2 μm and 1 μm.

The magnetic energy of a nanoparticle (E) is equal to the opposite of the scalar product of the magnetization of the nanoparticle (M) by the magnetic field (B) generated by said at least one magnetic layer according to the following formula:

$$E=-\vec{M}\cdot\vec{B}$$

where E is the magnetic energy of the nanoparticle (in Joule),

M is the magnetization of the nanoparticle (in Amperes per meter), and

B is the intensity of the magnetic field (in Tesla).

The magnetization in the case of materials having magnetic properties used in the invention is a strictly increasing function of the intensity of the magnetic field, so that the minimums of the magnetic energy of the nanoparticles correspond to the maximums of the standard of the magnetic field, and therefore to the capture zones.

When a magnetic nanoparticle is magnetized by the single magnetic field generated by said at least one magnetic layer, the capture zones are located at the junctions of a first and a second region.

The magnetic field generated by said at least one magnetic layer exhibits variations in intensity of at least 0.1 mT and at most 1 T, advantageously at least 0.1 mT and at most 500 mT, more advantageously of at least 0.5 mT and at most 300 mT, even more advantageously at least 1 mT and at most 200 mT.

These variations in the intensity of the magnetic field make it possible to generate a strong magnetic field gradient, that is to say, a sufficient magnetic field gradient to exert a significant capture force with respect to the Brownian motion of the nanoparticles. Thus, such a magnetic field gradient is localized. In addition, said gradient points to a capture zone and has a value of at least 10 $Tm^{-1}$ at a distance of 10 μm from said at least one magnetic layer, advantageously from 10 $T\cdot m^{-1}$ to $10^5$ $T\cdot m^{-1}$, even more advantageously from 500 $T\cdot m^{-1}$ to $5*10^3$ $T\cdot m^{-1}$. In this way, the strong magnetic field gradients guide the suspended nanoparticles toward the capture zone(s) of said at least one magnetic layer.

When the magnetic nanoparticles are captured by said at least one magnetic layer, they position themselves at the or each capture zone. This particular positioning is very interesting for directly detecting and quantifying the molecules captured, as will be described in more detail below.

The intensity of the magnetic field can be measured with a magneto-optic technique called MOIF (Magneto-Optical Imaging Film).

The MOIF technique is based on the Faraday effect. In general, this technique consists in immersing, in the magnetic field of an object whose intensity is to be measured, a flat film composed of a material whose optical properties are affected in a known manner by magnetic fields. Typically, said film is attached to said object. Said flat film has a width and a length at least equal to that of the zone of the tested object. Following this first step, said flat film is illuminated by a beam of light of known amplitude and polarization, this beam passing through said flat film. The analysis of the polarization and the amplitude of the light beam that has passed through said flat film provides a measurement of the planar components of the magnetic field present within it. An example measurement of the intensity of the magnetic field of an object by the MOIF technique is given by the article Grechishkin et al., *J. Appl. Phys.* 120, 174502 (2016).

In practice, a thin planar film, the thickness of which is typically less than one micrometer and which is composed of a magneto-optical material (for example a rare earth-based garnet), is deposited on a transparent non-magnetic substrate (for example glass, quartz or silica), then it is covered with a very thin reflecting layer, a mirror (for example made of gold, silver or aluminum), the thickness of which is less than 100 nm). Thus, the film of magneto-optical material compound is covered on one of its faces with a transparent non-magnetic substrate, and on the other face with a reflecting layer. This assembly is attached to an object emitting a magnetic field, such as a capture support according to the invention. Then, the film of magneto-optical material is illuminated with a beam of polarized light that first passes through the transparent non-magnetic layer (whose optical capacities are not influenced by the magnetic field of the magnetic object and which therefore has no incidence on the polarization of said beam), then passes through the film of optical material (whose magnetic field generated by the magnetic object affects the optical properties and which therefore has an incidence on the polarization of the beam), is reflected by the reflective layer, passes through the film of optical material again (which again affects the polarization of the beam), then again through the glass (which does not affect the polarization of the beam) before ending in the polarization analyzer. The angle of rotation of the polarization of the reflected beam relative to the incident beam is proportional to the magnetic field, to the Faraday coefficient of rotation of the garnet, and to the thickness of the magneto-optical material. A distribution of the intensity of the magnetic field generated by said at least one magnetic layer is thus obtained owing to the calibration curve, which represents the rotation by the Faraday effect of the light beam as a function of the intensity of the magnetic field. This curve is specific to the magneto-optical material used.

In particular, the intensity of the magnetic field can be measured by the MOIF technique using a MagView CMOS system marketed by the company MATESY GmbH with a model C sensor as polarization analyzer, using a garnet of the DLGi5 type as the film of magneto-optical material, the calibration curve of which is shown in FIG. 11. In this instrument, the mirror is replaced by a CMOS sensor so the light does not have to be reflected.

The results may be confirmed by numerical and analytical simulation, for example by one of the following two approaches:

- A finite element approach performed using the COMSOL Multiphysics® 5.0 modeling software). This software allows numerical simulations to be performed in a two-dimensional environment with a thickness of 10 mm. Upstream, the thickness and width of said at least one magnetic layer are measured on the one hand, typically optically using a bright-field microscopy image, and on the other hand its afterglow values or impact are measured; see below for more detail. These data are entered in the software, and the magnetic field generated by said at least one magnetic layer is simulated using the MFNC (Magnetic Field No Current) toolbox in a steady state.
- A so-called semi-analytical approach. The latter is based on the approach developed for example in the article by Chigirinsky S. et al, *Advanced Study Center Co. Ltd.*, 20 (2009), 85-91. Here also, upstream, the thickness and width of said at least one magnetic layer are measured on the one hand, and the remanence or retentivity values of said at least one magnetic layer are measured on the other hand. Said at least one magnetic layer is broken down into a sum of elements having a uniform magnetization, then an analytical resolution of the equations giving the magnetic field of each element is done for example using the Scilab® 6.02 software (publisher Scilab Enterprises). The field generated by each element of said at least one magnetic layer is added to that generated by all of the other elements of said at least one magnetic layer at each point in space. In the case where at least one additional magnetic field source is also present, see below for more detail, the magnetic field generated by said at least one additional source is added at each point to the total field generated by said at least one magnetic layer.

According to one embodiment of the invention, the second region comprises magnetic grains polarized in a second different direction deviated by at least 30° with respect to the first direction of polarization of the magnetic grains of the first region, advantageously deviated by 30° to 180°. In the invention, "from 30° to 180°" is understood to mean 30°, 31°, 32°, 33°, 34°, 35°, 36°, 37°, 38°, 39°, 40°, 41°, 42°, 43°, 44°, 45°, 46°, 47°, 48°, 49°, 50°, 51°, 52°, 53°, 54°, 55°, 56°, 57°, 58°, 59°, 60°, 61°, 62°, 63°, 64°, 65°, 66°, 67°, 68°, 69°, 70°, 71°, 72°, 73°, 74°, 75°, 76°, 77°, 78°, 79°, 80°, 81°, 82°, 83°, 84°, 85°, 86°, 87°, 88°, 89°, 90°, 91°, 92°, 93°, 94°, 95°, 96°, 97°, 98°, 99°, 100°, 101°, 102°, 103°, 104°, 105°, 106°, 107°, 108°, 109°, 110°, 111°, 112°, 113°, 114°, 115°, 116°, 117°, 118°, 119°, 120°, 121°, 122°, 123°, 124°, 125°, 126°, 127°, 128°, 129°, 130°, 131°, 132°, 133°, 134°, 135°, 136°, 137°, 138°, 139°, 140°, 141°, 142°, 143°, 144°, 145°, 146°, 147°, 148°, 149°, 150°, 151°, 152°, 153°, 154°, 155°, 156°, 157°, 158°, 159°, 160°, 161°, 162°, 163°, 164°, 165°, 166°, 167°, 168°, 169°, 170°, 171°, 172°, 173°, 174°, 175°, 176°, 177°, 178°, 179° or 180°.

Advantageously, the second region comprises magnetic grains polarized in a second different direction deviated by at least 60°, more advantageously deviated by at least 90°, still more advantageously deviated by at least 120°, even more advantageously deviated by at least 150°.

According to an advantageous embodiment of the invention, the second region comprises magnetic grains polarized in a second direction opposite the first direction of polarization of the magnetic grains of the first region, i.e. a polarization inversion of 180°.

According to another embodiment, the magnetic grains of the second region are not polarized. Such a configuration also allows the appearance of a variation in the intensity of the magnetic field and therefore a maximum of the standard of the intensity of the magnetic field generated by said at least one magnetic layer.

According to one embodiment of the invention, said at least one first region and said at least one second region have the same dimensions. Alternatively, they have different dimensions, in particular different widths and/or lengths.

According to one embodiment of the invention, said at least one first region and/or said at least one second region has a width ranging from 10 to 500 μm. In the invention, "from 10 to 500 μm," is understood to mean 10 μm, 20 μm, 30 μm, 40 μm, 50 μm, 60 μm, 70 μm, 80 μm, 90 μm, 100 μm, 110 μm, 120 μm, 130 μm, 140 μm, 150 μm, 160 μm, 170 μm, 180 μm, 190 μm, 200 μm, 210 μm, 220 μm, 230 μm, 240 μm, 250 μm, 260 μm, 270 μm, 280 μm, 290 μm, 300 μm, 310 μm, 320 μm, 330 μm, 340 μm, 350 μm, 360 μm, 370 μm, 380 μm, 390 μm, 400 μm, 410 μm, 420 μm, 430 μm, 440 μm, 450 μm, 460 μm, 470 μm, 480 μm, 490 μm, 500 μm.

Advantageously, said at least one first region and/or said at least one second region has a width advantageously ranging from 50 to 250 μm, more advantageously from 70 to 150 μm, even more advantageously from 90 to 110 μm.

According to one embodiment, said at least one first region and said at least one second region form the same pattern. This pattern can in particular correspond to a tape. Alternatively, they represent different patterns.

According to one embodiment, said at least one magnetic layer is coated with a protective film with a thickness of less than 1 μm. Such a film advantageously makes it possible to protect said at least one magnetic layer, without, however, hampering its capture/attraction capacities due to its very small thickness.

Said at least one magnetic layer can by itself constitute the capture support as such In this case, the latter advantageously has a thickness of at least 5 μm, and more advantageously of 10 to 20 μm.

Said magnetic layer is advantageously placed on a support member.

According to one embodiment of the invention, the material used for the support member is chosen from the following list: glass, silicon, a polymer of plastic material, organic material such as paper or bamboo, quartz, gold, an adhesive tape, a non-magnetic metal alloy such as dural or titanium, or a combination of these materials.

Advantageously, the polymer is chosen from the following list: polydimethylsiloxane (PDMS), polymethyl methacrylate (PMMA), a cyclo-olefin polymer (COP), a cyclo-olefin copolymer (COC), polycarbonate, polyimide, polyvinyl chloride (PVC), polyethylene, polypropylene, silicone, polyester, or a combination of these materials.

The support member can be a single layer of the material listed above.

The magnetic layer arranged on the support member can be stretched, for example using two winding spools like a VHS cassette.

According to one embodiment of the invention, the capture support comprises a capture receptacle configured to receive the sample containing the molecule to be captured and delimited by at least one wall comprising said at least one magnetic layer. This capture receptacle has, as the smallest dimension, a dimension of 20 μm to 1000 μm. In the invention, "from 20 μm to 1000 μm" is understood to mean 20 μm, 40 μm, 60 μm, 80 μm, 100 μm, 120 μm, 140 μm, 160 μm, 180 μm, 200 μm, 220 μm, 240 μm, 260 μm, 280 μm, 300 μm, 320 μm, 340 μm, 360 μm, 380 μm, 400 μm, 420 μm, 440 μm, 460 μm, 480 μm, 500 μm, 520 μm, 540 μm, 560 μm, 580 μm, 600 μm, 620 μm, 640 μm, 660 μm, 680 μm, 700 μm, 720 μm, 740 μm, 760 μm, 780 μm, 800 μm, 820 μm, 840 μm, 860 μm, 880 μm, 900 μm, 920 μm, 940 μm, 960 μm, 980 μm and 1000 μm.

According to one embodiment of the invention, the capture support is chosen from among a chamber, a parallelepipedal chamber, a hollow straight cylinder, a well, a well in the form of a straight cone, in particular of a truncated straight cone or truncated pyramid, a microfluidic channel, a titration plate, a test tube and a microtube.

In the case of a chamber and a parallelepipedal chamber, said at least one magnetic layer is arranged at one, and if several magnetic layers are present, at least one, wall of said chamber.

In the case of a hollow straight cylinder, said at least one magnetic layer is arranged at the circumferential wall of said cylinder.

In the case of a well, said at least one magnetic layer is arranged at one, and if several magnetic layers are present, at least one, wall of said well. Advantageously, said at least one magnetic layer is arranged at the wall forming the bottom of said well.

In the case of a well in the form of a cone, in particular of a truncated or truncated pyramidal straight cone, said at least one magnetic layer is arranged at one, and if several magnetic layers are present, at least one, wall of said well.

In the case of a microfluidic channel, said at least one magnetic layer is arranged at one, and if several magnetic layers are present, at least one, wall of said channel.

In the case of a titration plate comprising a plurality of wells, said at least one magnetic layer is arranged at one, and if several magnetic layers are present, at least one, wall of said at least one well. Advantageously, said at least one magnetic layer is arranged at the wall forming the bottom of said at least one well.

In the case of a test tube or a microtube, said at least one magnetic layer is arranged at one, and if several magnetic layers are present, at least one, wall of said test tube or microtube. Advantageously, said at least one magnetic layer is arranged at the circumferential wall of said test tube or microtube.

Said at least one magnetic layer may be fixed to the support. Advantageously, said fixing is irreversible. In this case, this fixing can be carried out for example by gluing, rolling or stamping. Alternatively, said fixing is reversible. Thus, said at least one magnetic layer may be fixed by a hook and loop system, more commonly called a velcro system, or else by a reversible glue, such as glue of animal origin.

The capture support may comprise one or more magnetic layers of the invention.

According to one embodiment, said at least one magnetic layer is folded over on itself, so that part of said magnetic layer is superimposed on another part.

According to one embodiment of the invention, said capture support comprises at least two magnetic layers. Advantageously, said magnetic layers are arranged on the same plane.

Alternatively, said magnetic layers are arranged on different planes, so that said two or at least two of the layers are superimposed on one another.

According to another embodiment of the invention, the capture support comprises at least one wall for attracting said magnetic nanoparticles, said wall comprising said at least one of the magnetic layers. Advantageously, the capture support comprises several attraction walls each having at least one magnetic layer and at least one of said walls is arranged on a different plane from the other magnetic layer(s); advantageously, at least one of said walls is superimposed on one or at least one of the other walls. Alternatively or in a complementary manner, at least one of said walls is arranged orthogonally to the other or to at least one of the other walls.

The use of the magnetic layers of the invention to capture nanometric magnetic particles is counterintuitive insofar as, commonly, these nanoparticles are captured by means of magnetic layers having strong magnetic properties, such as for example magnetic layers made of rare earth-based alloys. Indeed, to capture nanoparticles, which inherently exhibit weak magnetization, due to their small volume. It is customary to use magnetic layers with strong magnetic properties. Examples of such "strong" magnetic layers based on rare earths are described in particular in document WO2014111187. Strong magnetic layers exhibit a remanence of 0.7 T to 1.5 T and a coercive field of 600 kA/m to 2400 kA/m$^3$.

Said at least one magnetic layer according to the invention exhibits values 5 to 15 times lower for apparent remanence and retentivity. The coercive field of said at least one magnetic layer ranges from 10 to 400 kA/m$^3$.

The "apparent remanence" refers to the remanence of said at least one magnetic layer taken as a whole, and not of each of the magnetic grains constituting it.

The coercive field of a ferromagnetic material designates the intensity of the magnetic field that it is necessary to apply to a material having initially reached its magnetization at saturation in order to cancel the magnetization of the material.

Remanence is a material-intensive quantity, which measures the induction or density of magnetic flux that persists in a ferromagnetic material after it has been magnetized using a strong external magnetic field. Remanence is measured in Tesla (T). A sample of permanent magnetic material, previously magnetized, has a magnetic moment proportional to its volume and to the remanence of the material. A magnetic moment is a vector quantity that makes it possible to characterize the intensity of a magnetic source. The magnetic flux generated by this sample is proportional to its moment. This magnetic flux can be measured in a vibrating sample magnetometer (VSM), or an extraction magnetometer, or a SQUID magnetometer. Typically, a sufficiently strong magnetic field (typically 4 to 6 Tesla) is applied to the sample along its preferential magnetization axis to saturate its magnetization, then this so-called "saturation" magnetic field is stopped. The measurement of the flux generated by the sample under a zero magnetic field (0 T) after saturation gives the remanent magnetic moment of the sample. The remanence of the material is then obtained, which is equal to the moment of the sample divided by the volume of the sample.

According to one embodiment of the invention, said at least one magnetic layer has a remanence of less than or equal to 0.6 T, advantageously a remanence of 0.01 T to 0.6 T. In the invention, "from 0.01 T to 0.6 T" is understood to mean 0.01 T, 0.02 T, 0.03 T, 0.04 T, 0.05 T, 0.06 T, 0.07 T, 0.08 T, 0.09 T, 0.1 T, 0.11 T, 0.12 T, 0.13 T, 0.14 T, 0.15 T, 0.16 T, 0.17 T, 0.18 T, 0.19 T, 0.2 T, 0.21 T, 0.22 T, 0.23 T, 0.24 T, 0.25 T, 0.26 T, 0.27 T, 0.28 T, 0.29 T, 0.3 T, 0.31 T, 0.32 T, 0.33 T, 0.34 T, 0.35 T, 0.36 T, 0.37 T, 0.38 T, 0.39 T, 0.4 T, 0.41 T, 0.42 T, 0.43 T, 0.44 T, 0.45 T, 0.46 T, 0.47 T, 0.48 T, 0.49 T, 0.5 T, 0.51 T, 0.52 T, 0.53 T, 0.54 T, 0.55 T, 0.56 T, 0.57 T, 0.58 T, 0.59 T, 0.6 T.

More advantageously, said at least one magnetic layer exhibits a remanence of 0.01 T to 1, more advantageously from 0.02 T to 0.5 T, even more advantageously from 0.05 T to 0.2 T.

When the thickness of said magnetic layer or all of the magnetic layers is too thin, that is to say, when it has a width and/or a length much greater, at least 10 times greater, than its thickness, it then becomes difficult to determine the volume of the magnetic material and therefore to calculate its remanence. This is particularly the case with commercially available magnetic tapes where a thin magnetic layer rests on a substrate layer and, moreover, the boundary between these two layers is often difficult to assess due to industrial manufacturing processes. In this case, the retentivity of the magnetic layer or of the set of magnetic layers is instead measured. The retentivity is equal to the magnetic moment of the sample divided by the surface of the sample (and no longer its volume). The retentivity is expressed in unit of surface density of magnetic flux, that is to say, in pm·Gauss. Typically, a 2 mm×2 mm sample (typical size to fit into a laboratory magnetometer) is cut from the capture support to be tested. Its exact area is measured under an optical microscope. The procedure to be followed to obtain the resonance of the magnetic material is the same as for remanence, that is to say, its magnetization will be saturated in order to obtain its magnetic moment.

Thus, the invention also relates to a kit as defined above, in which said at least one magnetic layer has a retentivity of 2000 to 30,000 μm·Gauss. In the invention, "2000 to 30,000 μm·Gauss" is understood to mean 2000 μm·Gauss, 2500 μm·Gauss, 3000 μm·Gauss, 3500 μm·Gauss, 4000 μm·Gauss, 4500 μm·Gauss, 5000 μm·Gauss, 5500 μm·Gauss, 6000 μm·Gauss, 6500 μm·Gauss, 7000 μm·Gauss, 7500 μm·Gauss, 8000 μm·Gauss, 8500 μm·Gauss, 9000 μm·Gauss, 9500 μm·Gauss, 10,000 μm. Gauss, 11,000 μm·Gauss, 12,000 μm·Gauss, 13,000 μm·Gauss, 14,000 μm·Gauss, 15,000 μm·Gauss, 16,000 μm·Gauss, 17,000 μm·Gauss, 18,000 μm·Gauss, 19,000 μm·Gauss, 20,000 μm. Gauss, 21,000 μm·Gauss, 22,000 μm·Gauss, 23,000 μm·Gauss, 24,000 μm·Gauss, 25,000 μm·Gauss, 26,000 μm·Gauss, 27,000 μm·Gauss, 28,000 μm·Gauss, 29,000 μm·Gauss, 30,000 μm·Gauss.

According to one embodiment of the invention, said at least one magnetic layer has a retentivity of 5000 to 20,000 μm·Gauss, advantageously from 8000 to 14,000 μm·Gauss, more advantageously from 9000 to 11,000 μm·Gauss. The captured magnetic nanoparticles have, as their largest dimension, a dimension less than 1 μm.

By virtue of their dimensions, the magnetic particles used exhibit superparamagnetic properties.

The term "superparamagnetic" denotes the property of particles of ferromagnetic or ferrimagnetic material of small dimensions of randomly changing the direction of magnetization in the absence of an applied magnetic field, under the effect of thermal agitation.

The "superparamagnetic" character of magnetic particles implies that in the absence of an external exciting magnetic field, the magnetic particles have no net magnetic moment, so that they do not attract each other, thus preventing their agglomeration.

Compared to microparticles coupled to capture elements, nanoparticles coupled to capture elements exhibit much greater performance in terms of molecule capture, due in particular to a higher diffusion coefficient (multiplied by 10) and a greatly increased (multiplied by $10^3$) concentration (number of logs per $m^3$). However, the magnetic force of each of them is divided by $10^3$ (figures in the case of 1/10 reduced size).

According to one embodiment of the invention, the magnetic nanoparticles have, as their largest dimension, a dimension ranging from 50 nm to 500 nm, advantageously from 50 nm to 250 nm, more advantageously from 100 to 250 nm, even more advantageously from 150 to 200 nm.

According to one embodiment, the magnetic nanoparticles comprise from 10 to 90% iron, advantageously from 30 to 80%, more advantageously from 50 to 70% iron. The greater the quantity of iron contained in the nanoparticles, the greater their magnetization in the presence of an additional magnetic field and the stronger their attraction by said at least one magnetic layer. Thus, the greater the quantity of iron, the less it will be necessary to increase their magnetization so that they are attracted more quickly, as will be seen below.

According to one embodiment of the invention, the nanoparticles are encapsulated. They may be obtained in particular by copolymerization of iron oxide and of polystyrene. This encapsulation makes it possible to limit the release of iron from the nanoparticles. Indeed, such a release disrupts the detection and quantification of the captured molecule.

Magnetic nanoparticles may have any shape such as parallelepipedal, toric, spherical, etc. The nanoparticles may have a smooth or irregular surface. When they have an irregular surface, they have a so-called "potato-like" shape.

Advantageously, the magnetic nanoparticles are spherical and are then likened to "beads." The particles may therefore be referred to as "beads" even if their geometry is not a perfect sphere.

Preferably, said beads are monodispersed, the dimensional uniformity of the beads giving them identical properties and thus improving the diffusion of the beads for their capture by said at least one magnetic layer. "Monodisperse" means that the standard deviation of the average diameter of the beads is less than or equal to 40 nm over 200 nm, advantageously 20 nm over 200 nm.

In some cases, the beads are marketed in a form dispersed in a matrix with little or no magnetic material, such as a plastic polymer, silica ($SiO_2$), etc.

The beads are preferably biocompatible, that is to say, they have the ability not to interfere with, or to degrade, the biological medium in which they are used.

To allow the coupling of a capture element to the magnetic nanoparticles, the surface of the latter is functionalized, in particular with proteins A or G of *Staphylococcus aureus* or else by a carbodiimide If proteins A or G are used, the bond between the capture element and the nanoparticles will not be covalent, unlike the use of a carbodiimide.

Various capture elements can be coupled to the nanoparticles. According to one embodiment of the invention, the capture element is chosen from an antibody, a Fab fragment, a F(ab')2 fragment or a Fv fragment of an antibody, an antigen, a nucleic acid sequence, an organelle corresponding in particular to a vesicle, a cell, an aptamer or a bacterium.

An antibody or "immunoglobulin" is made up of 4 chains of amino acids, where we can distinguish two light chains and two so-called heavy chains. Each heavy chain is linked by a disulfide bridge to a light chain. In addition, the end of a heavy chain and that of the associated light chain together define a paratope owing to hypervariable regions. An antibody thus comprises two paratopes each allowing binding with an epitope of an antigen. The heavy chains are interconnected at a so-called hinge region.

The fragment of the antibody corresponding to one of the two paratopes is called Fragment Fv; it is the smallest fragment of an antibody retaining the recognition properties of an epitope.

The Fab fragment corresponds to an entire light chain and the end of the heavy chain linked to this light chain. A Fab fragment thus comprises a Fv fragment. There are two Fab fragments for an antibody.

The F(ab')2 fragment corresponds to the association of two Fab fragments linked together by the hinge region of the heavy chains.

The Fv, Fab and F(ab')2 fragments exhibit the same affinity for an antigen as the complete antibody.

A nucleic acid is a polymer whose basic unit is the nucleotide. A nucleic acid can be either deoxyribonucleic acid (DNA) or ribonucleic acid (RNA).

An organelle is a differentiated compartment contained in the cytoplasm of eukaryotic cells and in which specific biological functions are performed. In particular, among the organelles, we find the endoplasmic reticulum, the Golgi apparatus, mitochondria, lysosomes and peroxisomes.

A vesicle is a compartment present in the cytoplasm of a cell and made up of at least one lipid bilayer. The vesicles circulate in the cytosol and have various functions such as storage, transport, or the digestion of cellular waste.

A cell is a compartment making up living beings; it is limited by a membrane and comprises DNA on the one hand, which is necessary for its reproduction, and proteins on the other hand, which are necessary for its functioning.

An aptamer is a synthetic oligonucleotide, most often an RNA that is capable of binding a specific ligand and sometimes of catalyzing a chemical reaction on that ligand1. Aptamers are generally synthetic compounds, isolated in vitro from combinatorial libraries of a large number of compounds of random sequence by an iterative selection method called "systematic evolution of ligands by exponential enrichment" (SELEX). Further details on aptamer synthesis using the SELEX method can be found in the article "Aptamers and SELEX in Chemistry & Biology" (Chem Biol. 2014 Sep. 18; 21(9): pages 1055-8).

A bacterium is a single-celled prokaryotic microorganism comprising a single cytoplasmic compartment containing DNA. Thus, this DNA, unlike eukaryotic cells, is not isolated from the cytoplasm by a nucleus. Bacteria reproduce by simply dividing in half by fissiparity.

The type of capture element to be used will be easily adapted by those skilled in the art depending on the type of molecule to be captured.

The invention also relates to a kit as defined above further comprising at least one additional magnetic field source, said additional source being external to said at least one magnetic layer.

The magnetic field generated by said at least one additional magnetic field source will have several impacts on the elements of the kit that make it possible on the one hand to accelerate the capture of the nanoparticles by the capture support, and on the other hand to obtain more localized capture capture zones, that is to say, more precise, less wide, typically extending over a distance of less than 15 μm from the orthogonal projection on the surface of said magnetic layer.

On the one hand, applying the magnetic field of said at least one additional magnetic field source advantageously makes it possible to increase the magnetization of the magnetic nanoparticles and thus to accelerate, or even to trigger their capture by said at least one magnetic layer of the capture support.

On the other hand, the presence of an additional magnetic field of a standard greater than or equal to that of the magnetic field generated by said at least one magnetic layer is added to the magnetic field generated by said at least one magnetic layer so that, based on the orientation of the additional magnetic field, the amplitude of some energy sinks of the resulting total magnetic field is greater than that of the energy sinks of the only magnetic field generated by said at least one magnetic layer, which also participates in accelerating the capture of the nanoparticles.

The capture zones are enhanced, on the surface of the support, where the magnetic field generated above the junctions between first and second regions by said at least one magnetic layer follows the same axis and the same direction as the additional magnetic field. The standard of the total intensity of the magnetic field is thereby significantly increased. On the contrary, above the first and second regions, the standard of the resultant of the additional magnetic field with that generated by said at least one magnetic layer is not increased by as much, since they are not collinear. The maximums of the standard of the intensity of the magnetic field are therefore more strongly increased than the minimums; the amplitude of certain energy sinks is therefore accentuated. This on the one hand accelerates the capture on these capture zones, which are more strongly attracted by these energy sinks, and on the other hand decreases the extent of the capture zones, which are therefore geographically better defined and more precise.

When the magnetic field generated by said at least one additional source at a junction between first and second regions, at the surface of the support, is greater than the magnetic field generated by said at least one magnetic layer along the same axis but in an opposite direction, the capture zones are eliminated. Indeed, the standard of the intensity of the magnetic field generated at this level is no longer a maximum, and the energy of the nanoparticles is no longer minimized there.

In the particular case where the polarization of the first and second regions is opposite and parallel to the surface of the support, with the additional magnetic field going in the same direction as the magnetic field generated jointly by said first and second regions at their junction at the surface of the support, every other capture zone is reinforced and every other capture zone is weakened or even canceled for the reasons mentioned above.

When the additional field is greater than or equal to the magnetic field generated by said at least one magnetic field source, the capture zone is located at the point where the additional magnetic field has the same orientation and is in the same direction as the field generated by said at least one magnetic tape. The capture zones can then be offset from their initial position, as outlined below.

The magnetization of an object corresponds to a vector quantity that characterizes the magnetic behavior of said object on a macroscopic scale. It originates from the orbital magnetic moment and the magnetic spin moment of the electrons. It is measured in amps per meter, or sometimes in Tesla.

Advantageously, said at least one additional magnetic field source is chosen from among a permanent magnet, a coil, or an electromagnet.

When several magnetic field sources are present, they can be chosen from a combination of at least one permanent magnet, at least one coil and/or at least one electromagnet. In particular, they can be chosen from an assembly of permanent magnets, coils, electromagnets and an assembly combination of the latter.

The magnetic field sources can be arranged side by side in a plane, in particular linearly, or else in a three-dimensional shape. The magnetic field sources can be placed side by side. In the invention, "side by side" is understood to mean that the latter are contiguous or else spaced from one another. In particular, the magnetic field sources that are adjacent exhibit a polarization inversion.

A permanent magnet is an object made from a hard magnetic material that has acquired, artificially or naturally, the lasting property of generating a magnetic field. The peculiarity of a permanent magnet lies in the fact that its magnetic field, once acquired, is generated continuously without the need for any particular action. A hard magnetic material refers to a material whose remanent magnetization and coercive field are large, greater than 0.3 T and 250 kA/m, respectively.

The hard magnetic material can be chosen from a rare earth-based magnet, a transition metal alloy of the 3d (Fe, Co, Ni)-noble metal (Pt or Pd as the majority element) series, a ferrite magnet and a MnBi, MnAl, MnGa, FeGa, AlNiCo magnet. When the material is a rare earth magnet, it can be chosen from RFeB (where R consists of Nd, Pr, Tb, Dy or a mixture of several of these elements), SmCo or RCoCu (crystallographic structure of the ⅕ type), SmCoCuFe (crystallographic structures of the ⅐ or 2/17 type), RFeN (where R consists essentially of Sm).

For the remainder of the description, the term "permanent magnet" can be simply designated by "magnet."

When said at least one additional magnetic field source is a magnet, it is advantageously coupled to a soft ferromagnetic element, otherwise called "yoke" or "magnetic circuit." This soft ferromagnetic element extends the magnet and has a permeability greater than 100 S.I. ("international system," unitless), and a saturation of 1.6 to 2.4 T. Unlike hard ferromagnetic elements, soft ferromagnetic elements exhibit low remanent magnetization and a weak coercive field. Such a soft ferromagnetic element does not exhibit magnetization in the absence of an external magnetic field and makes it possible to channel the magnetic field lines of the magnet, and thus to increase the value of the magnetic field generated by the magnet.

A coil consists of a winding of conductive wire. This winding can optionally be produced around a ferromagnetic material called a core. As opposed to the magnet, a coil only emits a magnetic field when a particular action is applied, in this case when an electric current is applied and passes through the conductive wire. Therefore, once this electric current is no longer applied, no more magnetic field is generated.

When said at least one additional magnetic field source is a coil, it is advantageously a planar coil, i.e. all of the turns are in at least one plane, advantageously in 1 to 5 planes.

According to one embodiment of the invention, said at least one magnetic layer has two opposing surfaces, which are a capture surface and an opposite surface, and said at least one additional magnetic field source is a planar coil that is contiguous to the capture surface of said at least one magnetic layer. Thus, the planar coil at least partially covers the capture surface of said at least one magnetic layer. In such a case, the nanoparticles will be immobilized lace at least in part on the planar coil, at the capture zones.

An electromagnet produces a magnetic field when supplied with an electric current: it converts electrical energy into magnetic energy. It consists of a coil and a core and/or one or more pole pieces made from soft ferromagnetic material. Thus, as in the case of a coil, an electromagnet does not emit a magnetic field when no electric current passes through it.

Said at least one additional magnetic field source may or may not be attached to the capture support.

According to one embodiment of the invention, said at least one additional magnetic field source is fixed to the capture support. Advantageously, said fixing is reversible. Thus, this fixing can be achieved by clipping to the capture support. Alternatively, said fixing is irreversible. Thus, this fixing can be achieved by gluing to the support.

According to one embodiment of the invention, said at least one additional magnetic field source is configured to emit a uniform magnetic field.

Uniform means a magnetic field whose gradient is less than $100\ T\cdot m^{-1}$ along the magnetization axis of said at least one additional magnetic field source and less than $150\ T\cdot m^{-1}$ along an axis orthogonal to the magnetization axis on the surface of said at least one additional magnetic field source. In the invention, "less than $100\ T\cdot m^{-1}$" means $100\ T\cdot m^{-1}$, $90\ T\cdot m^{-1}$, $80\ T\cdot m^{-1}$, $70\ T\cdot m^{-1}$, $60\ T\cdot m^{-1}$, $50\ T\cdot m^{-1}$, $40\ T\cdot m^{-1}$, $30\ T\cdot m^{-1}$, $20\ T\cdot m^{-1}$, $10\ T\cdot m^{-1}$ or $0\ T\cdot m^{-1}$. In the invention, "less than $150\ T\cdot m^{-1}$" means $150\ T\cdot m^{-1}$, $140\ T\cdot m^{-1}$, $130\ T\cdot m^{-1}$, $120\ T\cdot m^{-1}$, $110\ T\cdot m^{-1}$, $100\ T\cdot m^{-1}$, $90\ T\cdot m^{-1}$, $80\ T\cdot m^{-1}$, $70\ T\cdot m^{-1}$, $60\ T\cdot m^{-1}$, $50\ T\cdot m^{-1}$, $40\ T\cdot m^{-1}$, $30\ T\cdot m^{-1}$, $20\ T\cdot m^{-1}$, $10\ T\cdot m^{-1}$ or $0\ T\cdot m^{-1}$.

The magnetic field generated by said at least one additional source may take any direction; advantageously, its direction is orthogonal to the surface of the support, more advantageously its direction and its sense are the same as those generated by said at least one magnetic layer, on the surface of the capture support at the junctions between the first and second regions.

Said at least one additional magnetic field source may be disposed at any position around the capture support. Thus, said at least one additional source can equally well be placed facing the capture surface of said at least one magnetic layer, or else facing its second surface. Alternatively, said at least one additional source may be placed at a distance from the capture support, opposite neither the first nor the second capture surface of said at least one magnetic layer.

Said at least one additional magnetic field source may have an area larger than the size of the area of said at least one magnetic layer that it is facing. In this sense, when said at least one magnetic field source is placed under the magnetic layer, its surface protrudes on either side of the magnetic layer. For example, when the additional magnetic field source is an assembly of magnets, part of the surface of one or at least one of the magnets is not facing said at least one magnetic layer or at least one magnet does not have a surface facing said at least one magnetic layer.

Indeed, in all cases, the significant effects brought about by this at least one magnetic field source are on the one hand the magnetization of the magnetic nanoparticles, and on the other hand the increase in the amplitude of the energy sinks, as indicated above.

Thus, said at least one additional magnetic field source is advantageously configured to generate a magnetic field of 1 mT to 400 mT at the nanoparticles when using the kit. In order to avoid a risk of demagnetization of the magnetic layer, it is advantageous for the value of the coercive field of said at least one additional magnetic field source to be at most 90% of the value of the coercive field of said at least one magnetic layer.

In the invention, “1 mT and 400 mT” means 1 mT, 5 mT, 10 mT, 15 mT, 20 mT, 25 mT, 30 mT, 35 mT, 40 mT, 45 mT, 50 mT, 55 mT, 60 mT, 65 mT, 70 mT, 75 mT, 80 mT, 85 mT, 90 mT, 95 mT, 100 mT, 105 mT, 110 mT, 115 mT, 120 mT, 125 mT, 130 mT, 135 mT, 140 mT, 145 mT, 150 mT, 155 mT, 160 mT, 165 mT, 170 mT, 175 mT, 180 mT, 185 mT, 190 mT, 195 mT, 200 mT, 205 mT, 210 mT, 215 mT, 220 mT, 225 mT, 230 mT, 235 mT, 240 mT, 245 mT, 250 mT, 255 mT, 260 mT, 265 mT, 270 mT, 275 mT, 280 mT, 285 mT, 290 mT, 295 mT, 300 mT, 305 mT, 310 mT, 315 mT, 320 mT, 325 mT, 330 mT, 335 mT, 340 mT, 345 mT, 350 mT, 355 mT, 360 mT, 365 mT, 370 mT, 375 mT, 380 mT, 385 mT, 390 mT, 395 mT, 400 mT.

Advantageously, said at least one magnetic field source is configured to generate a magnetic field of 10 mT to 400 mT, more advantageously of 50 mT to 200 mT.

According to one embodiment of the invention, said at least one additional magnetic field source is configured to emit a magnetic field continuously.

Alternatively, said at least one additional magnetic field source is configured to emit a pulsed magnetic field. Advantageously, the duration of a pulse is greater than or equal to 1 ms. Such a duration makes it possible to increase the magnetization of the magnetic nanoparticles for a sufficiently long period of time for their displacement to be influenced by it, compared to a simple Brownian movement.

The invention also relates to a kit as defined above where said at least one magnetic layer having a capture surface, said at least one magnetic layer is at least partially covered on said capture surface by a non-magnetic layer.

When such a non-magnetic layer is present, the capture and immobilization of the nanoparticles take place against the surface of the non-magnetic layer for the part of said at least one coated magnetic layer, due to the fact that the so-called “capture” surface of said at least one magnetic layer is coated.

The presence of this non-magnetic layer is advantageous in that it makes it possible to delay triggering of the attraction of the nanoparticles by the capture support at the desired moment, as will be seen in detail below.

According to one embodiment of the invention, the material of the non-magnetic layer is chosen from the following list: glass, silicon, a polymer of plastic material, silicone paper, an adhesive tape, a non-magnetic metal alloy such as dural or titanium, quartz, organic material such as paper or bamboo, wood, gold or a combination of these materials.

Advantageously, the polymer is chosen from the following list: polydimethylsiloxane (PDMS), polymethyl methacrylate (PMMA), a cycloolefin polymer (COC/COP), polycarbonate, polyimide, polyvinyl chloride (PVC), polyethylene, polypropylene, silicone, polyester, or a combination of these materials.

According to one embodiment, said non-magnetic layer has the same composition as that of the support member. Alternatively, said non-magnetic layer has a composition different from that of the support member.

Advantageously, said at least one magnetic field source does not exhibit fluorescence. Even more advantageously, it is opaque so as not to reflect light.

Advantageously, the material of the non-magnetic layer consists of or comprises an adhesive tape having a superposition of a layer of polyvinyl chloride (PVC) and of an adhesive layer or of a layer of polypropylene and of an acrylic glue.

According to one embodiment of the invention, said at least one magnetic layer is covered over at least 1% of its capture surface by said non-magnetic layer. “At least 1%” is understood to mean 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%.

Advantageously, said at least one magnetic layer is covered over at least 30% of its capture surface, more advantageously at least 50% of its capture surface, even more advantageously at least 60% of its capture surface, advantageously at least 80% of its capture surface.

According to one embodiment of the invention, the capture surface of said at least one magnetic layer is completely covered by said non-magnetic layer.

The invention also relates to a kit as defined above, in which said non-magnetic layer has a thickness of 1 to 300 µm. In the invention, “1 to 300 µm” is understood to mean 1 µm, 2 µm, 3 µm, 4 µm, 5 µm, 6 µm, 7 µm, 8 µm, 9 µm, 10 µm, 11 µm, 12 µm, 13 µm, 14 µm, 15 µm, 16 µm, 17 µm, 18 µm, 19 µm, 20 µm, 21 µm, 22 µm, 23 µm, 24 µm, 25 µm, 26 µm, 27 µm, 28 µm, 29 µm, 30 µm, 31 µm, 32 µm, 33 µm, 34 µm, 35 µm, 36 µm, 37 µm, 38 µm, 39 µm, 40 µm, 41 µm, 42 µm, 43 µm, 44 µm, 45 µm, 46 µm, 47 µm, 48 µm, 49 µm, 50 µm, 51 µm, 52 µm, 53 µm, 54 µm, 55 µm, 56 µm, 57 µm, 58 µm, 59 µm, 60 µm, 61 µm, 62 µm, 63 µm, 64 µm, 65 µm, 66 µm, 67 µm, 68 µm, 69 µm, 70 µm, 71 µm, 72 µm, 73 µm, 74 µm, 75 µm, 76 µm, 77 µm, 78 µm, 79 µm, 80 µm, 81 µm, 82 µm, 83 µm, 84 µm, 85 µm, 86 µm, 87 µm, 88 µm, 89 µm, 90 µm, 91 µm, 92 µm, 93 µm, 94 µm, 95 µm, 96 µm, 97 µm, 98 µm, 99 µm, 100 µm, 101 µm, 102 µm, 103 µm, 104 µm, 105 µm, 106 µm, 107 µm, 108 µm, 109 µm, 110 µm, 111 µm, 112 µm, 113 µm, 114 µm, 115 µm, 116 µm, 117 µm, 118 µm, 119 µm, 120 µm, 121 µm, 122 µm, 123 µm, 124 µm, 125 µm, 126 µm, 127 µm, 128 µm, 129 µm, 130 µm, 131 µm, 132 µm, 133 µm, 134 µm, 135 µm, 136 µm, 137 µm, 138 µm, 139 µm, 140 µm, 141 µm, 142 µm, 143 µm, 144 µm, 145 µm, 146 µm, 147 µm, 148 µm, 149 µm, 150 µm, 151 µm, 152 µm, 153 µm, 154 µm, 155 µm, 156 µm, 157 µm, 158 µm, 159 µm, 160 µm, 161 µm, 162 µm, 163 µm, 164 µm, 165 µm, 166 µm, 167 µm, 168 µm, 169 µm, 170 µm, 171 µm, 172 µm, 173 µm, 174 µm, 175 µm, 176 µm, 177 µm, 178 µm, 179 µm, 180 µm, 181 µm, 182 µm, 183 µm, 184 µm, 185 µm, 186 µm, 187 µm, 188 µm, 189 µm, 190 µm, 191 µm, 192 µm, 193 µm, 194 µm, 195 µm, 196 µm, 197 µm, 198 µm, 199 µm, 200 µm, 201 µm, 202 µm, 203 µm, 204 µm, 205 µm, 206 µm, 207 µm, 208 µm, 209 µm, 210 µm, 211 µm, 212 µm, 213 µm, 214 µm, 215 µm, 216 µm, 217 µm, 218 µm, 219 µm, 220 µm, 221 µm, 222 µm, 223 µm, 224 µm, 225 µm, 226 µm, 227 µm, 228 µm, 229 µm, 230 µm, 231 µm, 232 µm, 233 µm, 234 µm, 235 µm, 236 µm, 237 µm, 238 µm, 239 µm, 240 µm, 241 µm, 242 µm, 243 µm, 244 µm, 245 µm, 246 µm, 247 µm, 248 µm, 249 µm, 250 µm, 251 µm, 252 µm, 253 µm, 254 µm, 255 µm, 256 µm, 257 µm, 258 µm, 259 µm, 260 µm, 261 µm, 262 µm, 263 µm, 264 µm, 265 µm, 266 µm, 267 µm, 268 µm, 269 µm, 270 µm, 271 µm, 272 µm, 273

μm, 274 μm, 275 μm, 276 μm, 277 μm, 278 μm, 279 μm, 280 μm, 281 μm, 282 μm, 283 μm, 284 μm, 285 μm, 286 μm, 287 μm, 288 μm, 289 μm, 290 μm, 291 μm, 292 μm, 293 μm, 294 μm, 295 μm, 296 μm, 297 μm, 298 μm, 299 μm or 300 μm.

Advantageously, said non-magnetic layer has a thickness of 1 to 150 μm, more advantageously 5 μm to 100 μm, even more advantageously from 10 to 80 μm, advantageously from 30 to 60 μm.

The non-magnetic layer should be neither too thin nor too thick. Indeed, in the case where said non-magnetic layer is too thin, that is to say, less than 1 μm, it does not have a significant impact on attenuating the attraction of the nanoparticles by said at least one magnetic layer.

It should be noted that the thickness of the layer will depend on the retentivity of said at least one magnetic layer and on the width of the first and second regions. Those skilled in the art will easily be able to adapt the thickness of the magnetic layer as a function of the retentivity and width of the regions of said at least one magnetic layer.

Typically, for a magnetic layer with a retentivity of 12000 μm·G and whose first and second regions have a width of 50 μm, the non-magnetic layer will advantageously have a thickness of 20 to 60 μm. For magnetic layers of lower retentivity, the thickness of the magnetic layer should be reduced accordingly.

In the event that the non-magnetic layer is too thick (depending on the thickness and widths of the regions of said at least one magnetic layer), the strong magnetic field gradients will be hidden by this non-magnetic layer. Thus, the magnetic field at the surface of said non-magnetic layer will be uniform or non-existent depending on the case. The nanoparticles will then not be immobilized, or else will be immobilized randomly, not in a particular pattern, on the surface of the non-magnetic layer.

Applying the magnetic field of said at least one additional magnetic field source advantageously makes it possible in such a case to "reveal" the strong magnetic field gradients at the surface of the non-magnetic layer, by increasing the amplitude of the energy sinks. This aspect of the invention makes it possible to "trigger" the capture and immobilization of the nanoparticles at the capture zones, as will be seen in detail below.

The invention also relates to a capture support comprising several (from 1 to 100) microfluidic channels that have either an input common to at least some of the channels or an independent input for each channel, on the one hand, and at the outlet, one vent per channel or else one vent common to at least some of the channels, on the other hand. These microfluidic channels are bonded to a non-magnetic layer, which in turn is deposited on a magnetic layer bonded to a support member. The magnetic layer has been encoded beforehand with a magnetization along the horizontal plane of said magnetic layer and an orientation varying by 180° from one region to another. A centimeter or millimeter magnet made from Neodymium-Iron-Boron is used as an additional magnetic field source to apply an external magnetic field whose orientation and direction are the same as those of the magnetic layer at the junctions between the first and second regions.

The invention also relates to a method of capturing a molecule contained in a sample, said method comprising the following steps:

a) bringing said sample into contact with magnetic nanoparticles as defined above, so as to form at least one capture complex between said molecule and said at least one capture element coupled to said magnetic nanoparticles;

b) the attraction of said at least one capture complex as formed during step a) by the magnetic field generated by at least one magnetic layer of a capture support as defined above, so that said at least one capture complex is immobilized against said capture support at the at least one capture zone as defined above.

The aim of step a) of the present invention is to complex the molecules to be captured with the nanoparticles via the capture element, so that these complexed molecules can be indirectly attracted, via the nanoparticles, in a subsequent step b) by means of said at least one magnetic layer and, in fine, be captured by immobilization against the support.

For the remainder of the description, a capture complex may simply be referred to by the term "complex."

According to one embodiment of the invention, said capture element is an antibody or an antigen, such that said at least one capture complex formed during step a) is an immune complex.

In the invention, "sample" means any simple or complex fluid.

In the invention, "complex fluid" means a mixture in which two phases coexist: solid-liquid (suspensions or solutions of macromolecules such as polymers), solid-gas (granular), liquid-gas (foams) or liquid-liquid (emulsions). Complex fluids deviate from the classical linear Newtonian relationship between stress and shear rate. They exhibit unusual mechanical responses to the stress or strain applied due to the geometric constraints that the coexistence of the phases imposes. The mechanical response comprises transitions between solid-like behavior and fluid-like behavior as well as fluctuations. In particular, the sample may be a biological fluid such as blood, urine, lymph, plasma, serum, saliva, tears, semen, vaginal secretions, pus from a wound, gastric fluid or cerebrospinal fluid. The sample may also be a medium used in bioprocesses, such as a culture medium, or a purified or clarified culture medium.

In the invention, "simple fluid" means a Newtonian fluid whose mechanical behavior is characterized by a single function of temperature, viscosity, a measure of the "slide" of the fluid. A stress applied to a simple fluid is directly proportional to the strain rate. In particular, the sample can be deionized water. Deionized water has the advantage of greatly limiting, or even preventing, the formation of nanoparticle clusters.

According to one embodiment of the invention, once the sample is brought into contact with the nanoparticles during step a), it is placed at the capture support in order to allow the attraction of said at least one capture complex during step b).

Thus, the contacting step and the attraction step are carried out separately, so that the nanoparticles are not attracted by said at least one magnetic layer when they are brought into contact with the sample. This advantageously makes it possible to obtain a homogeneous distribution of the nanoparticles in the sample and therefore a more efficient complexation of the capture elements with the molecule to be captured.

Alternatively, the sample is first placed at the support before it is brought into contact with the nanoparticles during step a). Thus, steps a) and b) are carried out at the same place, that is to say, at the support. This embodiment is of great interest in certain applications, in particular because it does not require handling fluid via actuators of the micro-pump or micro-valve type.

According to one embodiment of the invention, between step a) and step b) a sonication is carried out of the mixture comprising the complexes of nanoparticles-molecules in suspension to be captured, with the aim of destroying any aggregate of complexes that may have been formed. These aggregates would indeed disrupt the quantification step seen below. This sonication can in particular be carried out at a frequency of at least 10000 Hz. The sonication can be continuous or pulsed. When the sonication is pulsed, the duration of each sonication can range from 200 to 700 milliseconds, in particular from 300 to 600 milliseconds, particularly 500 milliseconds, spaced from 1 to 6 seconds, in particular from 1 to 4 seconds, particularly 2 seconds. These sonication conditions allow the function of destroying the aggregates to be ensured while avoiding overheating of the medium, which could denature the capture elements, the molecules to be captured and the detection elements.

During step a), the concentration of the nanoparticles is advantageously from $10^6$ to $10^{11}$ particles/ml. In the invention, "from $10^6$ to $10^{11}$ particles/ml" means $10^6$ particles/ml, $10^7$ particles/ml, $10^8$ particles/ml, $10^9$ particles/ml, $10^{10}$ particles/ml and $10^{11}$ particles/ml.

A minimum concentration of $10^6$ particles/ml provides a sufficient concentration for an efficient capture of molecules to be captured dispersed in the sample. In addition, a maximum concentration of $10^{11}$ particles/ml makes it possible to avoid too great an agglomeration of the nanoparticles (cluster of diameter less than or equal to 15 μm), which on the one hand would disrupt the bond between the capture element and the molecule to be captured, and on the other hand would have a negative impact on the quantification of the captured molecule. A high concentration of nanoparticles would also be responsible for screening magnetic fields, that is to say, attenuating them, and would have a negative impact on the attraction of nanoparticles. In the invention, "cluster of diameter less than or equal to 15 μm" means 15 μm, 10 μm, 5 μm, 4, μm, 3 μm, 2 μm, 1 μm, 0.5 μm and 0.2 μm.

According to one embodiment, step a) further comprises bringing the sample into contact with an element for detecting said molecule.

This detection element has a marker that may be fluorescent, luminescent or colored so as to be recognized by an appropriate detection means. This marker may also be an enzyme with redox properties.

During step a), a so-called "sandwich" complex formed by a magnetic nanoparticle, the capture element, the molecule to be captured and the detection element is thus formed. The capture molecule is then surrounded, "sandwiched," by the capture element and the detection element.

The formation of these "sandwich" complexes, where the detection element is attached to the molecule to be captured from the first step, is made possible owing to the good diffusion characteristics in the mixture of magnetic nanoparticles. Thus, the formation of such complexes would be made more difficult with magnetic microparticles.

The sonication step mentioned above can also be carried out in this embodiment under the same conditions in order to avoid any aggregation of "sandwich" complexes.

Alternatively, the detection element can be placed in the presence of the molecule to be captured during a step c), following the immobilization against the support of the complexes formed by a nanoparticle, a capture element and a capture molecule. Therefore, the so-called "sandwich" complexes as described above are formed a posteriori during this step c).

Ultimately, at the end of step a), a mixture is obtained comprising complexes of nanoparticles, capture elements and molecules to be captured, or complexes of nanoparticles, capture elements, molecules to be captured and a detection element if such a detection element is present. In this mixture, molecules to be captured alone and nanoparticles coupled to the capture elements alone, and optionally detection elements alone, may remain.

Said mixture may be deposited, for example by means of a pipette, on a capture support in order to immobilize the nanoparticles during step b). Said mixture can also be injected into the capture support, in the case where this capture support is a chamber, for example.

Once said mixture is placed at the support, all of the magnetic nanoparticles (complexed or not) will be attracted by said at least one magnetic layer and will come to rest against the support, and more precisely against the capture surface of said at least one magnetic layer.

During their immobilization, the magnetic nanoparticles (complexed or not) are not distributed randomly against the support, and more precisely against the capture surface of said at least one magnetic layer.

In fact, the nanoparticles are immobilized at the capture zones as defined in the invention. Only a minority fraction of the nanoparticles, less than 15%, will therefore either be immobilized outside these capture zones or will not be captured.

Thus, the nanoparticles are distributed against the support, and more precisely against the capture surface of said at least one magnetic layer, according to a particular pattern defined by all of the junctions of the first and second regions.

This distribution is very interesting because it makes it possible to determine where the nanoparticles will be captured, which allows direct quantification of said captured molecules without going through a washing step.

The organization of the first and second regions of said at least one magnetic layer allows detection and quantification to be carried out without washing the support directly after the immobilization of the capture complexes and the binding with the detection elements or the immobilization of the "sandwiched" capture complexes.

To do this, it is first necessary to determine the quantity of marking at the capture zones, then that outside the capture zones.

Those skilled in the art will easily be able to adapt the means for determining the quantity of marking to be implemented as a function of the type of marker coupled to the detection elements. In particular, these means can be chosen from a spectrophotometer in scanning mode, an epifluorescence microscope, a confocal microscope, a two-photon microscope, the measurement of the redox activity of an enzyme, etc.

For example, in the context of fluorescence marking, those skilled in the art will benefit from using a fluorescence microscope equipped with a "GFP" cube (excitation 460-490 nm) or with a "PCR" cube (excitation 650 nm-emission 660 nm) coupled to a charge-coupled device (CCD) or CMOS camera, as presented in the "Examples" part of the present description.

The amount of marking outside the capture zones corresponds to "background signal." In other words, this marking corresponds to the detection elements not having coupled to the capture complexes and to the minority fraction of the complexes immobilized outside the capture zones, as well as to the effect of the matrix (residual signal of the medium).

In order to obtain the quantity of specific marking emitted at the capture zones, the quantity of marking obtained outside that of the capture zones is subtracted from that obtained at the capture zones.

The invention also relates to a capture method as defined above, where the attraction of said at least one capture complex during step b) is carried out by the joint action of the magnetic field generated by said at least one magnetic layer and by a magnetic field generated by at least one additional magnetic field source as defined above.

As mentioned above, said at least one additional magnetic field source makes it possible to increase, or even to saturate, the magnetization of the magnetic nanoparticles, and furthermore to increase the amplitude of the energy sinks, and thus to accelerate the attraction of the nanoparticles by said at least one magnetic layer.

Moreover, as discussed above, the additional magnetic field makes it possible to reinforce certain capture zones and thus promotes localized capture, which therefore favors detection without washing of the captured molecule, as described above.

This joint action also makes it possible to avoid the use of evaporation of the solvent from the sample aimed at bringing the nanoparticles closer to the capture support and thus accelerating their capture. Such an evaporation in fact requires heating the sample or a very long waiting time, which could have negative repercussions on the bond between the capture element/the detection element and the molecule to be captured, and therefore on the quantification of the molecule to be captured.

The attraction of the nanoparticles is therefore achieved by the joint action of said at least one magnetic field source and of said at least one magnetic layer, each exerting a different action and function.

Owing to its function and its action, said at least one magnetic field source can be placed anywhere with respect to the capture support, as mentioned above.

Thus, said at least one additional source may equally well be arranged facing the capture surface of said at least one magnetic layer and/or the non-magnetic layer, facing the opposite surface or the support member, or in any other position, laterally offset for example.

Significant magnetization of the nanoparticles is advantageously achieved by applying a magnetic field at their level of 1 mT to 400 mT, advantageously 10 mT to 400 mT, more advantageously from 50 mT to 200 mT.

The action of said at least one additional magnetic field source can be carried out throughout steps a) and b).

Advantageously, it is triggered during step b). Thus, during step a) and before triggering the action of said at least one additional magnetic field source, its magnetic field at the magnetic nanoparticles is insufficient or even zero.

The triggering of the action of said at least one additional field source during step b) is ensured by the generation of a magnetic field at the magnetic nanoparticles from 1 mT to 400 mT, advantageously 10 mT to 400 mT, more advantageously from 50 mT to 200 mT.

So as to trigger the action of said at least one additional magnetic field source, the latter can, according to a first alternative, be brought closer to the capture support. For this embodiment, said at least one additional magnetic field source is advantageously a permanent magnet.

According to a second alternative, this triggering is achieved by passing an electric current through said additional magnetic field source. For this embodiment, said at least one additional magnetic field source is advantageously a coil or an electromagnet, and the triggering is achieved by the passage of an electric current through said additional magnetic field source.

Advantageously, even if the action of said at least one additional magnetic field source is stopped at the end of step b), for example either by moving this source away or by stopping the passage of the electric current passing through it, the captured nanoparticles remain in place against the capture support at the capture zones. Thus, it is possible to move the capture support to an appropriate place to detect the marker of the detection elements, without the position of these nanoparticles being impacted, and therefore without a direct detection without a washing step being compromised.

The invention also relates to a capture method as defined above in which the capture support further comprises a non-magnetic layer as defined above, and in which the attraction of said at least one capture complex by the capture support during step b) is triggered by means of the magnetic field of said at least one additional magnetic field source.

In this embodiment, the presence of a non-magnetic layer reduces the possibility, or even prevents, that the nanoparticles are attracted only by the magnetic field generated by said at least one magnetic layer.

Thus, advantageously, on the one hand, the magnetic field generated by all of said at least one magnetic layer and of said at least one additional source has at least one variation in its intensity of at least 0.1 mT at a distance of at least 1 μm from the capture surface of said non-magnetic layer, said at least one variation in its intensity defining a maximum and a minimum of the standard of the intensity of the magnetic field, so as to define a capture zone of the magnetic nanoparticles on the capture support at said maximum of the standard of said magnetic field, and on the other hand, the magnetic field generated by said at least one magnetic layer does not exhibit at least one variation in its intensity of at least 0.1 mT at a distance of at least 1 μm from the surface of said non-magnetic layer, so that the magnetic field generated by only said at least one magnetic layer does not make it possible to define a capture zone of the magnetic nanoparticles on the surface of said non-magnetic layer.

The surface of the support corresponding to its surface against which the nanoparticles are immobilized.

Therefore, the attraction of the magnetic nanoparticles during step b) is contingent upon the action of said at least one magnetic field source on these nanoparticles, that is to say, by a significant increase in the magnetization of these particles by means of the magnetic field generated by this source, and/or an increase in the amplitude of energy sinks.

This aspect of the invention is very interesting because it makes it possible to optimize the execution of steps a) and b) in the same place, that is to say, at the capture support, by reducing, or even canceling out, the possibility that the nanoparticles can be attracted by the action of said at least one magnetic layer alone during step a).

Due to the presence of a non-magnetic layer, at least part of the nanoparticles (complexed or not) will not be immobilized against said at least one magnetic layer, but against this non-magnetic layer. More precisely, the non-magnetic layer having a capture surface and an opposite surface facing said at least one magnetic layer, at least part of the nanoparticles are immobilized during step b) against the first capture surface of the non-magnetic layer.

The invention also relates to a capture method as defined above in which the sample is placed at the capture support before step a) of bringing into contact with the magnetic nanoparticles.

Advantageously, the action of said at least one magnetic field source is triggered during step b).

Therefore, during step a), the magnetization of the magnetic nanoparticles and/or the amplitude of the energy sinks of said at least one magnetic layer are not sufficient to allow the attraction of said nanoparticles by the action of only said at least one magnetic layer covered by said non-magnetic layer. Thus, the mixing of the nanoparticles with the sample is disturbed little, if at all, by an early attraction by said at least one additional magnetic source.

Surprisingly, the inventors have discovered that despite the presence of a non-magnetic layer and its impact on the attractiveness of said at least one magnetic layer on the nanoparticles, if the action of the magnetic field generated by said at least one additional magnetic field source is stopped at the end of step b), for example either by moving this source away or by stopping the electric current, the immobilized nanoparticles remain in place against the support at the capture zones.

One explanation of the phenomenon would be that the gradients of magnetic fields produced by said at least one magnetic layer and present on the surface of the non-magnetic layer would be sufficient to hold the nanoparticles in place against said non-magnetic layer. An additional explanation would be that there is an adsorption, that is to say, a chemical/physical bonding, between on the one hand the magnetic nanoparticles that have agglomerated with one another and, on the other hand, the particles absorbed with the capture surface of the non-magnetic layer.

Thus, here again, it is possible to move the capture support to an appropriate place to detect the marker of the detection elements, without the position of these particles being impacted, and therefore without a direct detection without a washing step being compromised.

The invention also relates to a capture method as defined above comprising a subsequent step c) of displacing the magnetic nanoparticles, which have been captured against the support, into a recovery zone.

This displacement is carried out using a technique called "connecting rod-crank," in which:

- the crank is the magnetic field generated by the magnetic regions of said at least one magnetic layer; we denote this magnetic field b(R) (R being a point in space). Said at least one magnetic layer exhibits a variation in the intensity of the generated magnetic field, so as to create magnetic energy minima,
- the connecting rod is a spatially uniform magnetic field (in direction and in intensity) generated by said at least one additional magnetic field source. In this application, the amplitude and the orientation of said magnetic field can be modified.

The "uniform" magnetic field generated by the connecting rod is applied over the entire zone where the magnetic field of the crank is generated. Thus, the magnetic field generated by the connecting rod coexists in space with the magnetic field generated by said at least one magnetic layer, so that their vector values are superimposed linearly in a medium of relative permeability equal to one (such as air or water).

Due to the fact that the magnetic field generated by the connecting rod can be modulated, it is possible during step c) to rotate it by at least 1° clockwise or counterclockwise around at least one axis of rotation and/or to amplify said magnetic field. Therefore, it is possible to temporally change the magnetic field of the connecting rod. Thus, we note the magnetic field of the connecting rod B(t) (t being the time).

Consequently, the magnetic field of the crank varies in space, but not in time, and that of the connecting rod varies in time.

Therefore, in the zone where the connecting rod and crank are applied, the total magnetic field ST is the vector sum of b and B, or $B_T(R,t)=b(R)+B(t)$.

In this way, it is possible during step c) to modify the position of the capture zones of the magnetic nanoparticles against the support.

In the invention, "from 1° to 360°" means 1°, 2°, 3°, 4°, 5°, 6°, 7°, 8°, 9°, 10°, 11°, 12°, 13° 14°, 15°, 16°, 17°, 18°, 19°, 20°, 21°, 22°, 23°, 24°, 25°, 26°, 27°, 28°, 29°, 30°, 31° 32°, 33°, 34°, 35°, 36°, 37°, 38°, 39°, 40°, 41°, 42°, 43°, 44°, 45°, 46°, 47°, 48°, 49° 50°, 51°, 52°, 53°, 54°, 55°, 56°, 57°, 58°, 59°, 60°, 61°, 62°, 63°, 64°, 65°, 66°, 67°, 68°, 69°, 70°, 71°, 72°, 73°, 74°, 75°, 76°, 77°, 78°, 79°, 80°, 81°, 82°, 83°, 84°, 85°, 86°, 87°, 88°, 89°, 90°, 91°, 92°, 93°, 94°, 95°, 96°, 97°, 98°, 99°, 100°, 101°, 102°, 103°, 104°, 105°, 106°, 107°, 108°, 109°, 110°, 111°, 112°, 113°, 114°, 115°, 116°, 117°, 118°, 119°, 120°, 121°, 122°, 123°, 124°, 125°, 126°, 127°, 128°, 129° 130°, 131°, 132°, 133° 134° 135°, 136°, 137°, 138°, 139°, 140°, 141°, 142°, 143° 144°, 145°, 146°, 147° 148° 149°, 150°, 151°, 152°, 153°, 154°, 155°, 156°, 157° 158°, 159°, 160°, 161° 162° 163°, 164°, 165°, 166°, 167°, 168°, 169°, 170°, 171° 172°, 173°, 174°, 175° 176° 177°, 178°, 179°, 180°, 181°, 182°, 183°, 184°, 185° 186°, 187°, 188°, 189° 190° 191°, 192°, 193°, 194°, 195°, 196°, 197°, 198°, 199° 200°, 201°, 202°, 203° 204° 205°, 206°, 207°, 208°, 209°, 210°, 211°, 212°, 213° 214°, 215°, 216°, 217° 218° 219°, 220°, 221°, 222°, 223°, 224°, 225°, 226°, 227° 228°, 229°, 230°, 231° 232° 233°, 234°, 235°, 236°, 237°, 238°, 239°, 240°, 241°, 242°, 243°, 244°, 245°, 246°, 247°, 248°, 249°, 250°, 251°, 252°, 253°, 254°, 255°, 256°, 257°, 258°, 259°, 260°, 261°, 262°, 263°, 264°, 265°, 266°, 267°, 268°, 269°, 270°, 271°, 272°, 273°, 274°, 275°, 276°, 277°, 278°, 279°, 280°, 281°, 282°, 283°, 284°, 285°, 286°, 287°, 288°, 289°, 290°, 291°, 292°, 293°, 294°, 295°, 296°, 297°, 298°, 299°, 300°, 301°, 302°, 303°, 304°, 305°, 306°, 307°, 308°, 309°, 310°, 311°, 312°, 313°, 314°, 315°, 316°, 317°, 318°, 319°, 320°, 321°, 322°, 323°, 324°, 325°, 326°, 327°, 328°, 329°, 330°, 331°, 332°, 333°, 334°, 335°, 336°, 337°, 338°, 339°, 340°, 341°, 342°, 343°, 344°, 345°, 346°, 347°, 348°, 349°, 350°, 351°, 352°, 353°, 354°, 355°, 356°, 357°, 358°, 359° or 360°.

A vector summation result of the magnetic fields of the connecting rod and the crank is then obtained which is different from that obtained at the end of step b), and the location of the maximums of the standard of the intensity of the magnetic field generated by the connecting rod and crank assembly is moved, so that the capture zones are offset with respect to this step b). Thus, the nanoparticles, attracted by the magnetic field gradients generated, are moved at the same time until they are positioned at the new position of the capture zones.

Advantageously, step c) is repeated in the same direction of rotation until the nanoparticles, being progressively displaced in the same direction, reach the recovery zone.

By repeating step c), a "conveyor belt" effect is obtained, where the nanoparticles are moved in the same direction along the surface of the capture support toward a recovery zone. Since the molecule to be captured is complexed with the nanoparticles, it is also recovered in this recovery zone.

Ultimately, owing to the invention, it is possible to recover the molecule to be captured without applying a fluidic flow to the support that would displace all of the molecules contained in the mixture.

The invention further relates to a use of a kit as defined above for the capture of a molecule contained in a sample, advantageously for the capture and detection of a molecule contained in a sample.

The invention also relates to a use of a magnetic layer for attracting nanoparticles having as largest dimension a dimension less than 1 μm, said magnetic layer comprising a juxtaposition, possibly repeated, of at least a first and a second region, the first region comprising magnetic grains polarized in a first direction, and the second region comprising magnetic grains that are non-polarized or polarized in a second direction different from the first direction of polarization of the magnetic particles of the first region, so that said one magnetic layer generates a magnetic field having at least one variation in its intensity of at least 0.1 mT at a distance of at least 1 μm from said at least one magnetic layer, said at least one variation in its intensity defining a maximum and a minimum of the standard of said intensity of the magnetic field, so as to define, at said maximum of the standard of said magnetic field, a capture zone of magnetic nanoparticles on said magnetic layer, and said nanoparticles each being coupled to at least one capture element of a molecule.

Another kit is also described for capturing a molecule contained in a sample comprising:

a) magnetic nanoparticles having a dimension of less than 1 μm as largest dimension, said nanoparticles each being coupled to at least one capture element, said at least one capture element specifically binding to said molecule, and b) a support for capturing said magnetic nanoparticles comprising or consisting essentially of at least one magnetic layer, said magnetic layer comprising a juxtaposition, possibly repeated, of at least a first and a second region, the first region comprising magnetic particles polarized in a first direction, and the second region comprising magnetic particles that are non-polarized or polarized in a second direction different from the first direction of polarization of the magnetic particles of the first region, so that said at least one magnetic layer generates a magnetic field not exhibiting at least one variation in its intensity of at least 0.1 mT at a distance of at least 1 μm from said at least one magnetic layer, c) at least one additional magnetic field source, so that the magnetic field generated by the assembly of said at least one magnetic layer and said at least one additional source exhibits at least one variation in its intensity of at least 0.1 mT at a distance of at least 1 μm from said at least one magnetic layer, said at least one variation of its intensity defining a maximum and a minimum of the standard of the intensity of said magnetic field, so as to define, at said maximum of the standard of said magnetic field, a zone for capturing magnetic nanoparticles on the capture support.

Advantageously, said additional source is external to said at least one magnetic layer.

Again advantageously, said at least one magnetic layer having a capture surface, said at least one magnetic layer is at least partially covered on said capture surface by a non-magnetic layer, and the magnetic field generated by all of said at least one magnetic layer and said at least one additional source exhibits at least one variation in its intensity of at least 0.1 mT at a distance of at least 1 μm from the capture surface of said non-magnetic layer, said at least one variation of its intensity defining a maximum and a minimum of the standard of the intensity of said magnetic field, so as to define, at said maximum of the standard of said magnetic field, a zone for capturing magnetic nanoparticles on the capture support.

All of the features described above relating to the capture support, the additional magnetic field source and the nanoparticles relating to the kit described above apply mutatis mutandis to this kit.

The invention also relates to a method for capturing a molecule contained in a sample, said method comprising the following steps:

a) bringing said sample into contact with magnetic nanoparticles as defined above, so as to form at least one capture complex between said molecule and said at least one capture element coupled to said magnetic nanoparticles;

b) the attraction of said at least one capture complex as formed during step a) by the magnetic field generated by an assembly of at least one magnetic layer of a capture support and at least one additional magnetic field source as defined above, so that said at least one capture complex is immobilized against said capture support at the at least one capture zone as defined above.

The invention also relates to a use of a kit as defined above for the capture of a molecule contained in a sample, advantageously for the capture and detection of a molecule contained in a sample.

The invention finally relates to a use of an assembly comprising a magnetic layer and an additional field source for attracting nanoparticles having a dimension of less than 1 μm as largest dimension, said magnetic layer comprising a juxtaposition, possibly repeated, of at least a first and a second region, the first region comprising magnetic grains polarized in a first direction, and the second region comprising magnetic grains that are non-polarized or polarized in a second direction different from the first direction of polarization of the magnetic particles of the first region, so that the magnetic field generated by all of said one magnetic layer and said additional source exhibits at least one variation in its intensity of at least 0.1 mT at a distance of at least 1 μm from said at least one magnetic layer, said at least one variation of its intensity defining a maximum and a minimum of the standard of the intensity of said magnetic field, so as to define, at said maximum of the standard of said magnetic field, a zone for capturing magnetic nanoparticles on said magnetic layer.

Advantageously, said nanoparticles are each coupled to at least one capture element of a molecule.

EXAMPLES

Example 1: Capture of Nanoparticles by a Magnetic Strip

The capture of nanoparticles by a magnetic strip of a magnetic card was tested first.

Experimental Protocol

The nanoparticles used (Chemicell nanoscreenmag ARA 200 nm) have an average diameter of 200 nm, a density of 1.25 g/cm$^3$, a saturation magnetization of 420,000 A/m, a mass concentration of 25 mg/ml, a length emission wavelength of 476 nm and an excitation wavelength of 490 nm. The nanoparticles are diluted in ddH$_2$O to a level of 1.1×10$^{\wedge 12}$ nanoparticles/g and 4.4×10$^9$ nanoparticles/ml.

In order to break up the aggregates of nanoparticles that may be present, the solution of nanoparticles diluted in deionized water (ddH$_2$O) was mixed using a SONIC RUPTOR 4000 sonicator. Intermittent sonication was produced within a tube at 20% of the total power of 400 W and an estimated frequency around 20000 Hz. A total of 3 sonication pulses were emitted with a duration of 500 milliseconds every 2 seconds.

In order to verify that the nanoparticles to be captured are not in the form of clusters of nanoparticles, the inventors have measured the size of the nanoparticles in solution by "Diffraction Light Scattering." The results are given in FIG. 15.

The capture support is a magnetic card made up of a PVC support member and a magnetic strip made up of three magnetic layers arranged on the same plane and made up of high coercivity magnetic polymers. The support member and the magnetic layers were assembled according to the ISO 7811 standard. The magnetic layers are each encoded with a succession of "1" corresponding to 182 times the LETTER F in Hexadecimal using an MSR605 encoder, which allows the magnetic field orientations to be varied by 180 degrees approximately every 55 μm.

The capture of the nanoparticles is carried out by depositing 5 μl of the solution of nanoparticles and depositing a drop on the magnetic layers of the magnetic card.

A schematic view of this capture is shown in FIG. 1. In this figure, nanoparticles 1 are in solution, and some 1' are attracted by a magnetic layer 3 of the magnetic strip (represented by black arrows). The magnetic layer has first 5 and second 7 regions whose grain polarization is reversed (represented by large white arrows). The magnetic field generated by each of the regions is represented by small white arrows that follow arcs starting on one side of a region and ending on the other side. The direction of these arrows indicates the direction of the generated magnetic field. The intensity of the field is represented by a color scale. This intensity of the magnetic field was obtained by the finite element approach carried out using the COMSOL Multiphysics® 5.0 modeling software, as described above. A white color indicates a strong intensity of the magnetic field. Above the magnetic layer 3, the intensity of the magnetic field generated by the first and second regions (5, 7) is visible, each of which is about 100 μm wide, the field exhibiting variations. The presence of maximums of the intensity of the magnetic field 9 can be clearly seen above the junctions between a first region 5 and a second region 7, and a lower intensity of the magnetic field at each region (5, 7) itself. At each maximum of the standard of the magnetic field 9, a capture zone 11 is thus defined by orthogonal projection on the surface of the magnetic layer 3, and at which the nanoparticles 1' will be immobilized.

Then, images are captured with a fluorescence microscope (Olympus BX41 M) equipped with a "GFP" cube (excitation 460-emission 490 nm) coupled to a CCD camera (Diagnostic Instruments SPOT RT Monochrome Digital Camera). A blue excitation light source (460-490 nm) is used. Images are captured with a total magnification of 50× and with a capture time of 3 seconds (Gain 14 db). An example of an image capture can be seen in FIG. 2. In this figure, the white dots represent the nanoparticles. An ordering of the captured nanoparticles can be clearly seen.

The percentage of nanoparticles captured by the magnetic strip is quantified by following the protocol described in the publication by Fratzl et al, Soft Matter (14) 2671-2680 (2018). Briefly, this quantification is obtained by the ratio of the area covered by the nanoparticles to the area not covered by the nanoparticles.

The results of the capture kinetics are shown in FIG. 7 and represented by curve B.

Results

As can be seen in FIG. 7, the capture of the magnetic nanoparticles is triggered instantly after depositing the drop on the magnetic substrate, and reaches 40% in 2 minutes.

Furthermore, the results shown in FIG. 15 show a single peak with suspended beads exhibiting an average diameter of 282 nm (9.5 nm standard deviation), corresponding to the diameter of a single nanoparticle. These results demonstrate that the nanoparticles are independent of each other and do not form clusters.

Example 2: Capture of Nanoparticles by a Magnetic Strip Covered with a Non-Magnetic Layer This example tests the capture of nanoparticles by a magnetic strip of a magnetic card covered with a non-magnetic layer.

Experimental Protocol

The nanoparticles used and the capture support are the same as those used in Example 1, except that the magnetic strip is covered by a self-adhesive layer of black polymer (Vinyl) 60 μm thick.

The method for capturing the nanoparticles, as well as the determination of the percentage of nanoparticles captured, are the same as those of Example 1.

A diagram of this capture is shown in FIG. 3. This view includes the elements shown in FIG. 1. In addition, a non-magnetic layer 13 is arranged on the surface of the magnetic layer 3. As can be seen in this FIG. 3, only a part of the magnetic fields generated by the magnetic layer 3 protrudes on the surface of the non-magnetic layer 13, so that the maximums of the standard of the magnetic field are "hidden" by the non-magnetic layer. There is therefore no variation in the intensity of said magnetic field of at least 0.1 mT at a distance of at least 1 μm from the surface of the capture support, and therefore no capture zones. The nanoparticles are therefore very weakly attracted, immobilized in a random manner against the magnetic strip and very predominantly remain in solution.

A photo of the capture result obtained is visible in FIG. 4, in which the white dots represent the nanoparticles. The ordering visible in FIG. 2 has disappeared in this figure.

The results of the capture kinetics are shown in FIG. 7, and represented by curve C.

Results

As can be seen in FIG. 7, the nanoparticles are captured very slowly by the magnetic strip of the magnetic card. After 10 minutes, the capture reaches only 15%.

Example 3: Capture of Nanoparticles by a Magnetic Strip Covered with a Non-Magnetic Layer in the Presence of an Additional Magnetic Field Source This example tests the capture of nanoparticles by a magnetic strip of a magnetic card covered with a non-magnetic layer in the presence of an additional magnetic field source.

Experimental Protocol

The nanoparticles used and the capture support are the same as those used in Example 2.

The additional magnetic field source is a head-to-tail assembly (vertical/horizontal magnetization) of NdFeB macro-magnets (N35, adhesion force of 800 g) parallelepipedal (20×10×1 mm), magnetized along the 1 mm axis.

The magnetic card is deposited on the additional magnetic field source so that the magnetic layers are not arranged opposite said source.

The method for capturing the nanoparticles, as well as the determination of the percentage of nanoparticles captured, are the same as those of Example 1.

A diagram of this capture is shown in FIGS. 5*a* and 5*b*. In FIG. 5*a*, the additional magnetic field source (not shown) emits a magnetic field with a direction perpendicular to the magnetic layer 3, represented by a white arrow with a black border. In FIG. 5*b*, the additional magnetic field source (not shown) emits a magnetic field with a direction parallel to the magnetic layer 3, represented by a white arrow with a black border. These two figures make it possible to see the effect of the direction of the magnetic field generated by the additional field source on the position of the capture zones.

These views show the elements presented in FIGS. 1 and 3. These figures clearly show on the one hand that the intensity of the magnetic field generated at the surface of the non-magnetic layer 13 is much stronger and that the maximums of the standard of the intensity of the magnetic field 9 are no longer hidden by the non-magnetic layer 13. Moreover, only every other maximum of the standard of the intensity of the magnetic field 9 is present compared to those initially shown in FIG. 1, and therefore every other capture zone 11 is present. However, these maximums 9 have an intensity greater than those initially shown in FIG. 1.

In FIG. 5*a*, with an additional magnetic field perpendicular to the magnetic layer 3, the capture zones 11 lie above the junctions toward which the polarization of the adjacent regions (5, 7) is oriented. However, the standard of the field is minimized above the junctions for which the polarization of the adjacent regions moves away.

It is interesting to note in FIG. 5*b* that with an additional magnetic field with a direction parallel to the magnetic layer 3, the capture zones 11 and the maximums of the standard of the intensity of the magnetic field 9 have been displaced and no longer arranged at the junctions between first and second regions (5, 7), but at the first regions 5 themselves.

A photo of the capture result obtained is visible in FIG. 6, in which the white dots represent the nanoparticles. Unlike FIG. 4, where there was no capture ordering, a new ordering appears in FIG. 6, different from that obtained in FIG. 2. Here, the nanoparticles form regularly arranged parallel bands, and we see that there are few nanoparticles present outside these bands.

The results of the capture kinetics are shown in FIG. 7, and represented by curve A.

Results

In this example, the capture of the magnetic nanoparticles is triggered immediately upon application of the external field. The capture is close to 100% in 2 minutes.

By combining the present result with that of Example 2, it can be concluded that it is possible to trigger the immobilization and the very rapid capture (2 minutes) of the nanoparticles when the magnetic strip is covered with a non-magnetic layer, by triggering the magnetic field of the additional source.

Example 4: Capture and Quantification of a Capture Element Coupled to Nanoparticles Finally, the detection and quantification of several concentrations of anti-mouse ovalbumin antibodies (capture element) coupled to magnetic nanoparticles were tested.

Each measurement is carried out by keeping the number of detection antibodies (anti-mouse antibodies) and total nanoparticles identical, but varying the quantity of nanoparticles coupled to the anti-mouse ovalbumin antibodies (by supplementing with nanoparticles coupled to ovalbumin).

Experimental Protocol

The nanoparticles used (Carboxyl Adem beads 200 nm (ref. 02120—Ademtech)) have a diameter of 200 nm, an approximate density of 2.0 g/cm$^3$, an approximate saturation magnetization of 40 emu/g, an approximate iron oxide content of 70% and a solid content of 30 mg/ml (3%). The nanoparticles are covered with COOH carboxylic functions with a density greater than 350 μmol/g.

The capture support is a magnetic card composed of a PVC support member on which three magnetic layers rest that are arranged on the same plane and composed of high coercivity magnetic polymers. The support member and the magnetic layers were assembled according to the ISO 7811 standard. The magnetic layers are each encoded with a succession of 1s using an MSR605 encoder, as shown in Example 1.

The additional magnetic field source is a head-to-tail assembly of NdFeB macro-magnets (N35, Adhesion force of 800 g) parallelepipedal (20×10×1 mm), magnetized along the 1 mm axis.

The capture element is an anti-ovalbumin (IgG) antibody produced in mice. These antibodies are grafted onto the nanoparticles at a final concentration of 10 μg/ml to 50 μg/ml.

The grafting on the nanoparticles at a final concentration of 10 μg/mL is carried out by the following protocol:

- activation of 90 μg of nanoparticles (i.e. 3 μl of Ademtech 30 mg/ml stock solution of Ademtech nanoparticles)) with a 25 μl solution containing EDC (10 mg/ml) and NHS (10 mg/ml);
- incubation for 15 minutes at room temperature with stirring;
- removal of the supernatant by capturing the nanoparticles using a centimeter magnet. This centimeter magnet is a neodymium magnetic cylinder, nickel-plated, 10 mm in diameter and 40 mm high;
- addition of a solution of 25 μl of anti-mouse ovalbumin antibody at a concentration of 1 mg/ml (i.e. 25 μg);
- incubation for 2 h at room temperature with stirring;
- removal of the supernatant by capturing the nanoparticles using a centimeter magnet as mentioned above; and
- suspension of the nanoparticles in a solution of 50 μL of PBS-Tween 0.05%—BSA (1 mg/ml). Nanoparticles functionalized with anti-ovalbumin antibody are obtained at a potential concentration of 500 μg/ml.

The other part of the nanoparticles is grafted with Ovalbumin (OVA). The grafting is carried out according to the same protocol as that described above with the difference that instead of adding a solution of 25 μl of anti-ovalbumin antibody, 25 μl of OVA are added at a concentration of 1 mg/ml (i.e. 25 μg).

The detection element is an antibody directed specifically against mouse antibodies (therefore against the anti-ovalbumin antibody) and is coupled to an Alexa 488 fluorochrome (Max excitation=490 nm; Max emission=525 nm) for detection.

FIG. 8 shows anti-mouse antibodies 15 carrying a fluorochrome 17 and coupled to the nanoparticle complexes 19 grafted by the antiovalbumin antibodies 21. Also shown is a nanoparticle 19 grafted with OVA 23 used for testing the specificity of the interaction between the antibodies.

The detection and quantification of anti-mouse ovalbumin antibodies is carried out by the following protocol:

in a 0.5 ml tube, mixture of 4.5 μg of nanoparticles previously grafted with anti-ovalbumin antibodies and/or with OVA); 2 μl of anti-mouse detection antibody (for a final concentration of 1 μg/ml) and 20 μl of PBS;
incubation for 15 minutes at ambient temperature in the 0.5 mL tube;
removing 5 μl of the solution and depositing a drop on the magnetic layers of the magnetic card; and
depositing the magnetic card on the additional magnetic field source, so that the PVC support member is arranged between the magnetic layers and the additional magnetic field source.

Five different conditions are met:

1) 4.5 μg of nanoparticles grafted with anti-mouse ovalbumin antibodies (i.e. an approximate anti-ovalbumin antibody concentration of 50 μg/ml);
2) 2.25 μg of nanoparticles grafted with anti-mouse ovalbumin antibodies and 2.25 μg nanoparticles grafted with ovalbumin (i.e. an approximate anti-ovalbumin antibody concentration of 25 μg/ml);
3) 1.125 μg of nanoparticles grafted with anti-mouse ovalbumin antibodies and 2.25 μg nanoparticles grafted with ovalbumin (i.e. an approximate anti-ovalbumin antibody concentration of 12.5 μg/ml);
4) 0.625 μg of nanoparticles grafted with anti-mouse ovalbumin antibodies and 2.25 μg nanoparticles grafted with ovalbumin (i.e. an approximate anti-ovalbumin antibody concentration of 6.25 μg/ml);
5) 4.5 μg of nanoparticles grafted to ovalbumin (i.e. a zero anti-ovalbumin antibody concentration);

Then, image captures of the magnetic layers of the magnetic card are taken with a fluorescence microscope (Olympus BX41 M) equipped with a "GFP" cube (excitation 460-490 nm) coupled to a CCD camera (Diagnostic Instruments SPOT RT Monochrome Digital Camera). A blue excitation light source (460-490 nm) is used. Images are captured with a total magnification of 50× and with a capture time of 5 seconds (Gain 1).

FIG. 10 shows the images obtained after capture. It is clearly observed that the nanoparticles coupled to the mouse antibody, which in turn is coupled to the anti-mouse antibody, are captured along capture zones in the form of bands. FIG. 10A to 10E respectively correspond to conditions 1) to 5) as described above. The amount of anti-mouse antibody detected is degressive for conditions 1) to 5), which is consistent with the amount of anti-ovalbumin antibody used in each condition. Condition 5 is a negative control, as no capture antibody is present. These results also agree with those obtained in FIG. 9.

The fluorescent signal is quantified by calculating the respective areas corresponding to the fluorescence peaks on the capture zones from which the general "background signal" is subtracted that is measured between the capture zones. In fact, unlike Examples 1 to 3 where the nanoparticles were fluorescent, here all the fluorescence detected not only corresponding to the captured molecules (the anti-ovalbumin antibodies in the present case), but also to the detection elements that remained in solution. It is then necessary to subtract the fluorescence emitted by these "free" detection elements from that emitted by the detection elements coupled to the captured molecule.

Taking the example of the capture shown in FIG. 10, the total fluorescence of the areas of the capture zones is measured in the form of fluorescent bands, from which the fluorescence measured between these areas is subtracted.

The fluorescence quantification is obtained in arbitrary units (AU)

The results obtained are shown in FIG. 9.

Results

As shown in FIG. 9, the fluorescence quantification of the capture zones obtained is proportional to the concentration of anti-ovalbumin antibodies that were added to the mixture ($R^2$=0.97).

From the fluorescence signal quantification method used (specific signal in the capture zones and non-specific signal outside it), these results make it possible to conclude that the nanoparticles coupled to a detection element are indeed captured in the capture zones.

However, these results make it possible to conclude that it is possible to quantify the number of molecules captured without a washing step between the immobilization of the nanoparticles and the detection of the detection element.

Example 5: Capture of Nanoparticles by Microfluidic Chambers

The nanoparticles used are the same as those used in Example 1, and were diluted 500 times in deionized water ($ddH_2O$) to achieve a concentration of 50 μg/mL.

The sonication step is also carried out.

The capture support comprises 18 microfluidic chambers each having an independent inlet and a vent at the outlet. Each microfluidic chamber is 6 mm long, 2.4 mm wide, and has a depth of 240 micrometers. The chambers are aligned next to each other with a pitch of 4.5 mm so as to form a bar. The microfluidic chambers are glued to a magnetic layer, which in turn is glued to a PVC support member. The support member and the magnetic layer were assembled according to the ISO 7811 standard. The magnetic layer is encoded with a succession of "1" corresponding to 182 times the LETTER F in Hexadecimal using an MSR605 encoder, which makes it possible to vary the magnetic field orientations by 180 degrees approximately every 55 μm.

6 microliters of the nanoparticle solution were injected into each of these microfluidic chambers. The chambers were filled one by one. After each filling, the capture was visualized with an epifluorescence microscope with a 10× magnification objective. A film was generated with a frame rate of 1.12 frames per second. The images obtained at times 0, 10, 30, 80 and 120 seconds of the recording are shown in FIG. 12.

Results

Despite the substantial depth of the microfluidic chambers, approaching 300 μm, it can be seen in FIG. 12 that the nanoparticles are well captured at the bottom of the microfluidic chambers (sets of aligned white dots), from 10 seconds of capture.

Example 6: Capture of Nanoparticles by Microfluidic Chambers in the Presence of an Additional Magnetic Field Source The nanoparticles and the capture support used are the same as in Example 5.

In addition, the capture support is based on a head-to-tail assembly (vertical magnetization) of 20 NdFeB macromagnets (Supermagnete, reference Q-10-04-02-N), parallelepipedal (10×4×2 mm), magnetized along the 2 mm axis and having an energy product of 50 megaGauss Oersted. The 20 magnets are arranged side by side with a pitch of 0.5 mm along the 4 mm axis so as to form a bar. 18 of the 20 magnets are placed below each of the 18 microfluidic chambers, and 2 are placed on each side.

6 microliters of the nanoparticle solution were injected into each of these microfluidic chambers. The chambers were filled one by one. After each filling, the capture was visualized with an epifluorescence microscope with a 10× magnification objective. A film was generated with an image capture at the rate of 1.12 frames per second. The images obtained at time 0, 2, 5, 12, 34 and 60 seconds are shown in FIG. 13.

The percentage of nanoparticles captured by the microfluidic chambers is quantified by following the protocol described in the publication by Fratzl et al, Soft Matter (14) 2671-2680 (2018). Capture kinetics were performed in triplicate in 3 different chambers. The results of the capture kinetics are shown in FIG. 14.

Results

As for Example 5, the nanoparticles are well captured at the bottom of the microfluidic chambers. By analogy with Examples 1 and 3, the capture of the nanoparticles is much faster here than in Example 5, without an external magnetic field source. In addition, as can be seen in FIG. 13, every other capture zone shown in FIG. 12 has disappeared (the spacing between each line of dots has doubled in FIG. 13), due to the external magnetic field generated by the assembly of the macro-magnets.

The capture kinetics data shown in FIG. 14 show that the capture of the nanoparticles is complete after 15 seconds.

The invention claimed is:

1. A kit for capturing a molecule contained in a sample comprising:

a) magnetic nanoparticles, each magnetic nanoparticle being free from one another, having a largest dimension of less than 1 μm, said nanoparticles each being coupled to at least one capture element, said at least one capture element specifically binding to said molecule, and b) a support for capturing and immobilizing said magnetic nanoparticles on a surface of the support, comprising at least one magnetic layer, said at least one magnetic layer being a flexible magnetic tape comprising magnetic composite materials randomly distributed in a polymer or else oriented along an axis in the polymer, said at least one magnetic layer comprising a direct juxtaposition, possibly repeated, of at least a first region and a second region, the first region comprising magnetic particles polarized in a first direction, and the second region comprising magnetic particles that are non-polarized or polarized in a second direction different from the first direction, the first direction and the second direction being opposite to each other and parallel to the surface of the support, wherein said at least one magnetic layer generates a magnetic field having at least one variation in intensity of at least 0.1 mT at a distance of at least 1 μm from said at least one magnetic layer, said at least one variation in intensity defining a maximum and a minimum of the standard of the intensity of said magnetic field, so as to define, at said maximum of the standard of said magnetic field, a capture zone for capturing and immobilizing the magnetic nanoparticles on the capture support, and said capture zone further comprising a non-magnetic layer which attenuates the magnetic field of the at least one magnetic layer, the kit further comprising at least one additional magnetic field source, said additional magnetic field source being external to said at least one magnetic layer, the additional magnetic field source generating an additional magnetic field to the magnetic field generated by the at least one magnetic layer.

2. The kit according to claim 1, wherein said at least one magnetic layer has a retentivity of 2000 μm Gauss to 30,000 μm Gauss.

3. The kit according to claim 1, wherein said non-magnetic layer has a thickness of 1 μm to 300 μm.

4. A method of capturing a molecule contained in a sample, said method comprising the following steps:

a) providing a kit comprising:

i) magnetic nanoparticles, each magnetic nanoparticle being free from one another, having a largest dimension of less than 1 um, said nanoparticles each being coupled to at least one capture element, said at least one capture element specifically binding to said molecule, and ii) a support for capturing and immobilizing said magnetic nanoparticles on a surface of the support, comprising at least one magnetic layer, said at least one magnetic layer being a flexible magnetic tape comprising magnetic composite materials randomly distributed in a polymer or else oriented along an axis in the polymer, said at least one magnetic layer comprising a direct juxtaposition, possibly repeated, of at least a first region and a second region, the first region comprising magnetic particles polarized in a first direction, and the second region comprising magnetic particles that are non-polarized or polarized in a second direction different from the first direction, the first direction and the second direction being opposite to each other and parallel to the surface of the support, wherein said at least one magnetic layer generates a magnetic field having at least one variation in intensity of at least 0.1 mT at a distance of at least 1 μm from said at least one magnetic layer, said at least one variation in intensity defining a maximum and a minimum of the standard of the intensity of said magnetic field, so as to define, at said maximum of the standard of said magnetic field, a capture zone for capturing and immobilizing the magnetic nanoparticles on the capture support, and said capture zone further comprising a non-magnetic layer which attenuates the magnetic field of the at least one magnetic layer, the kit further comprising at least one additional magnetic field source, said additional magnetic field source being external to said at least one magnetic layer, the additional magnetic field source generating an additional magnetic field to the magnetic field generated by the at least one magnetic layer, b) bringing said sample into contact with magnetic nanoparticles from said kit, so as to form at least one capture complex between said molecule and said at least one capture element coupled to said magnetic nanoparticles, each nanoparticles being dispersed freely from one another in the sample;

c) attraction of said at least one capture complex as formed during step b) by the magnetic field generated by at least one magnetic layer of the capture support from said kit, so that said at least one capture complex is immobilized against said capture support at an at least one capture zone, and wherein the non-magnetic layer from said capture zone attenuates the magnetic field of the at least one magnetic layer of the capture support, the attraction of said at least one capture complex by the capture support during step c) being triggered by means of the magnetic field of said at least one additional magnetic field source from said kit, and wherein the attraction of said at least one capture complex during step c) is carried out by the joint action of the magnetic field generated by said at least one magnetic layer and by the magnetic field generated by the at least one additional magnetic field source.

5. The method according to claim 4, wherein the capture support further comprises a non-magnetic layer having a thickness of 1 to 300 μm.

6. The method according to claim 5, wherein the sample is placed at the capture support before step b) of bringing into contact with the magnetic nanoparticles.

7. A method of capturing a molecule contained in a sample, comprising;

providing a kit comprising:

i) magnetic nanoparticles, each magnetic nanoparticle being free from one another, having a largest dimension of less than 1 um, said nanoparticles each being coupled to at least one capture element, said at least one capture element specifically binding to said molecule, and ii) a support for capturing and immobilizing said magnetic nanoparticles on a surface of the support, comprising at least one magnetic layer, said at least one magnetic layer being a flexible magnetic tape comprising magnetic composite materials randomly distributed in a polymer or else oriented along an axis in the polymer, said at least one magnetic layer comprising a direct juxtaposition, possibly repeated, of at least a first region and a second region, the first region comprising magnetic particles polarized in a first direction, and the second region comprising magnetic particles that are non-polarized or polarized in a second direction different from the first direction, the first direction and the second direction being opposite to each other and parallel to the surface of the support, wherein said at least one magnetic layer generates a magnetic field having at least one variation in intensity of at least 0.1 mT at a distance of at least 1 μm from said at least one magnetic layer, said at least one variation in intensity defining a maximum and a minimum of the standard of the intensity of said magnetic field, so as to define, at said maximum of the standard of said magnetic field, a capture zone for capturing and immobilizing the magnetic nanoparticles on the capture support, and said capture zone further comprising a non-magnetic layer which attenuates the magnetic field of the at least one magnetic layer, the kit further comprising at least one additional magnetic field source, said additional magnetic field source being external to said at least one magnetic layer, the additional magnetic field source generating an additional magnetic field to the magnetic field generated by the at least one magnetic layer, and bringing a sample into contact with magnetic nanoparticles from said kit.

8. The kit according to claim 1, wherein the support comprises a capture receptacle to receive the sample containing the molecule to be captured, the capture receptable being delimited by at least one wall comprising said at least one magnetic layer and having a depth between 60 μm to 1000 μm.

9. The kit according to claim 1, wherein the magnetic nanoparticles have a largest dimension in a range of 50 nm to 500 nm.

10. The kit according to claim 1, wherein the magnetic nanoparticles have a largest dimension in a range of 100 nm to 250 nm.

11. The kit according to claim 1, wherein said at least one magnetic layer has a retentivity of 9000 μm Gauss to 11,000 μm Gauss.

12. The kit according to claim 1, wherein said at least one magnetic layer generates a magnetic field having at least one variation in intensity of 1 mT to 200 mT at a distance of at least 1 um from said at least one magnetic layer, and said at least one additional magnetic field source generates a magnetic field of 50 mT to 200 mT.

13. The kit according to claim 1, wherein said capture zone is completely covered by the non-magnetic layer.

14. The kit according to claim 1, wherein said non-magnetic layer has a thickness of 30 μm to 60 μm.

* * * * *